United States Patent
Richard et al.

(10) Patent No.: US 8,961,941 B2
(45) Date of Patent: Feb. 24, 2015

(54) COMPOSITION COMPRISING A DIBENZOYLMETHANE SCREENING AGENT AND A MEROCYANINE DICYANO OR CYANOACETATE DERIVATIVE; METHOD FOR THE PHOTOSTABILIZATION OF THE DIBENZOYLMETHANE SCREENING AGENT

(75) Inventors: Herve Richard, Gagny (FR); Benoit Muller, Paris (FR)

(73) Assignee: L'Oreal, Paris (FR)

( * ) Notice: Subject to any disclaimer, the term of this patent is extended or adjusted under 35 U.S.C. 154(b) by 80 days.

(21) Appl. No.: 13/634,176

(22) PCT Filed: Mar. 7, 2011

(86) PCT No.: PCT/EP2011/053378
§ 371 (c)(1),
(2), (4) Date: Nov. 27, 2012

(87) PCT Pub. No.: WO2011/113719
PCT Pub. Date: Sep. 22, 2011

(65) Prior Publication Data
US 2013/0064871 A1    Mar. 14, 2013

Related U.S. Application Data

(60) Provisional application No. 61/282,735, filed on Mar. 24, 2010.

(30) Foreign Application Priority Data

Mar. 15, 2010 (FR) .................................. 10 51819
Oct. 22, 2010 (FR) .................................. 10 58686

(51) Int. Cl.
*A61Q 17/04* (2006.01)
*A61K 8/00* (2006.01)
*A61K 8/35* (2006.01)
*A61K 8/41* (2006.01)
*A61K 8/44* (2006.01)
*C07C 45/86* (2006.01)
*C07C 255/30* (2006.01)
*C07D 211/46* (2006.01)

(52) U.S. Cl.
CPC . *A61Q 17/04* (2013.01); *A61K 8/35* (2013.01); *A61K 8/41* (2013.01); *A61K 8/44* (2013.01); *C07C 45/86* (2013.01); *C07C 255/30* (2013.01); *C07D 211/46* (2013.01); *A61K 2800/52* (2013.01); *C07C 2101/14* (2013.01)
USPC ............................................. 424/59; 424/401

(58) Field of Classification Search
None
See application file for complete search history.

(56) References Cited

FOREIGN PATENT DOCUMENTS

| EP | 1 864 648 A1 | 12/2007 |
|---|---|---|
| WO | WO-2004/006878 A1 | 1/2004 |
| WO | WO-2006/125676 A1 | 11/2006 |
| WO | WO-2008/090066 A2 | 7/2008 |

*Primary Examiner* — Bethany Barham
(74) *Attorney, Agent, or Firm* — Novak Druce Connolly Bove + Quigg LLP

(57) ABSTRACT

The present invention relates to a cosmetic composition comprising the combination i) of at least one screening agent of the dibenzoylmethane derivative type and ii) of at least one specific merocyanine dicyano or cyanoacetate derivative. It also relates to a method for the photostabilization, with regard to radiation, of at least one screening agent of the dibenzoylmethane derivative type by an effective amount of at least one specific merocyanine dicyano or cyanoacetate derivative.

20 Claims, No Drawings

COMPOSITION COMPRISING A DIBENZOYLMETHANE SCREENING AGENT AND A MEROCYANINE DICYANO OR CYANOACETATE DERIVATIVE; METHOD FOR THE PHOTOSTABILIZATION OF THE DIBENZOYLMETHANE SCREENING AGENT

CROSS REFERENCE TO RELATED APPLICATIONS

This application is a National Phase filing under 35 U.S.C. §371 of PCT/EP2011/053378 filed on Mar. 7, 2011; and this application claims priority to Application No. 1051819 filed in France on Mar. 15, 2010 under 35 U.S.C. §119, and this application claims priority to Application No. 1058686 filed in France on Oct. 22, 2010 under 35 U.S.C. §119; and this application claims the benefit of U.S. Provisional Application No. 61/282,735 filed on Mar. 24, 2010; the entire contents of each application is hereby incorporated by reference.

The present invention relates to a cosmetic composition comprising the combination i) of at least one screening agent of the dibenzoylmethane derivative type and ii) of at least one specific merocyanine dicyano or cyanoacetate derivative, the definition of which will be given below.

It also relates to a method for the photostabilization, with regard to radiation, of at least one screening agent of the dibenzoylmethane derivative type by an effective amount of at least one specific merocyanine dicyano or cyanoacetate derivative, the definition of which will be given below.

It is known that light radiation with wavelengths of between 280 nm and 400 nm makes possible browning of the human epidermis and that rays with wavelengths more particularly of between 280 and 320 nm, known under the name of UV-B, cause erythemas and skin burns which may be harmful to the development of natural tanning. For these reasons, and for aesthetic reasons, there exists a constant demand for means for controlling this natural tanning for the purpose of thus controlling the colour of the skin; it is thus advisable to screen out this UV-B radiation.

It is also known that UV-A rays, with wavelengths of between 320 and 400 nm, which cause browning of the skin, are capable of bringing about a detrimental change in the latter, in particular in the case of sensitive skin or of skin continually exposed to solar radiation. UV-A rays cause in particular a loss in the elasticity of the skin and the appearance of wrinkles, resulting in premature skin ageing. They promote the triggering of the erythemal reaction or accentuate this reaction in some subjects and can even be the cause of phototoxic or photoallergic reactions. Thus, for aesthetic and cosmetic reasons, such as the preservation of the natural elasticity of the skin, for example, increasingly people desire to control the effect of UV-A rays on their skin. It is therefore desirable also to screen out UV-A radiation.

With the aim of providing protection of the skin and keratinous substances against UV radiation, use is generally made of antisun compositions comprising organic screening agents which are active in the UV-A region and which are active in the UV-B region. The majority of these screening agents are fat-soluble.

In this respect, a particularly advantageous family of UV-A screening agents is currently composed of dibenzoylmethane derivatives and in particular 4-(tert-butyl)-4'-methoxydibenzoylmethane, this being because these exhibit a high intrinsic absorption power. These dibenzoylmethane derivatives, which are now products well known per se as screening agents active in the UV-A region, are described in particular in French Patent Applications FR-A-2326405 and FR-A-2440933, and in European Patent Application EP-A-0114607; furthermore, 4-(tert-butyl)-4'-methoxydibenzoylmethane is currently provided for sale under the trade name of "Parsol 1789®" by DSM Nutritional Products.

Unfortunately, it is found that dibenzoylmethane derivatives are products which are relatively sensitive to ultraviolet radiation (in particular UV-A radiation), that is to say, more specifically, that they exhibit an unfortunate tendency to decompose more or less rapidly under the action of the latter. Thus, this substantial lack of photochemical stability of dibenzoylmethane derivatives in the face of the ultraviolet radiation to which they are by nature intended to be subjected does not make it possible to guarantee continuous protection during prolonged exposure to the sun, so that repeated applications at regular and close intervals of time have to be carried out by the user in order to obtain effective protection of the skin against UV rays.

Patent Application WO 0128732 reveals a method for the photostabilization of a dibenzoylmethane derivative by a merocyanine phenyl sulphone derivative. On the one hand, this photostabilization of the dibenzoylmethane derivative by the merocyanine phenyl sulphone derivative is not completely satisfactory. On the other hand, these merocyanine phenyl sulphone derivatives exhibit the disadvantage of decomposing in the presence of dibenzoylmethane under the influence of UV radiation.

Provision has already been made, in Patent Application WO 2008090066, to photostabilize dibenzoylmethane derivatives by cyclic derivatives of merocyanine cyanoacetate. Here again, the photostabilization of the dibenzoylmethane derivative remains inadequate and these merocyanine cyanoacetate derivatives also exhibit the disadvantage of decomposing in the presence of dibenzoylmethane.

The photostabilization of dibenzoylmethane derivatives with regard to UV radiation thus constitutes a problem which to date has not been solved in a completely satisfactory manner.

In point of fact, the Applicant Company has now just discovered, surprisingly, that, by combining the abovementioned dibenzoylmethane derivatives with at least one specific merocyanine dicyano or cyanoacetate derivative, the definition of which will be given below, it is possible to substantially further improve the photochemical stability (or photostability) of these same dibenzoylmethane derivatives and their effectiveness in the UV-A region without the disadvantages indicated above.

This discovery forms the basis of the present invention.

Thus, in accordance with one of the subject-matters of the present invention, a composition is now provided comprising, in a cosmetically acceptable vehicle, at least one UV screening system, characterized in that it comprises:
(i) at least one dibenzoylmethane derivative and
(ii) at least one merocyanine dicyano or cyanoacetate derivative, the definitions of which will be given below.

Another subject-matter of the invention is also a method for improving the chemical stability with regard to UV radiation of at least one dibenzoylmethane derivative which consists in combining the said dibenzoylmethane derivative with an effective amount of at least one merocyanine dicyano or cyanoacetate derivative, the definitions of which will be given below.

Other characteristics, aspects and advantages of the invention will become apparent on reading the detailed description which will follow.

"Cosmetically acceptable" is understood to mean compatible with the skin and/or its superficial body growths, exhibiting a pleasant colour, a pleasant odour and a pleasant feel, and not causing unacceptable discomfort (smarting, tightness, redness) liable to dissuade the consumer from using this composition.

"Effective amount" is understood to mean an amount sufficient to produce a notable and significant improvement in the photostability of the dibenzoylmethane derivative or derivatives in the cosmetic composition. This minimum amount of merocyanine dicyano or cyanoacetate derivative as described in detail later, which can vary according to the nature of the vehicle selected for the composition, can be determined without any difficulty by means of a conventional test for measuring photostability, such as that given in the examples below.

Mention may in particular be made, among the dibenzoylmethane derivatives, without implied limitation, of:
2-methyldibenzoylmethane,
4-methyldibenzoylmethane,
4-isopropyldibenzoylmethane,
4-(tert-butyl)dibenzoylmethane,
2,4-dimethyldibenzoylmethane,
2,5-dimethyldibenzoylmethane,
4,4'-diisopropyldibenzoylmethane,
4,4'-dimethoxydibenzoylmethane,
4-(tert-butyl)-4'-methoxydibenzoylmethane,
2-methyl-5-isopropyl-4'-methoxydibenzoylmethane,
2-methyl-5-(tert-butyl)-4'-methoxydibenzoylmethane,
2,4-dimethyl-4'-methoxydibenzoylmethane,
2,6-dimethyl-4-(tert-butyl)-4'-methoxydibenzoylmethane.

Use will in particular be made, among the abovementioned dibenzoylmethane derivatives, of 4-isopropyldibenzoylmethane, sold under the name of "Eusolex 8020" by Merck, which corresponds to the following formula:

Preference is very particularly given to the use of 4-(tert-butyl)-4'-methoxydibenzoylmethane or Butyl Methoxy Dibenzoylmethane or avobenzone, provided for sale under the trade name of "Parsol 1789" by DSM Nutritional Products Inc.; this screening agent corresponds to the following formula:

The dibenzoylmethane derivative or derivatives can be present in the compositions in accordance with the invention at contents which preferably vary from 0.01 to 20% by weight, more preferably from 0.1 to 10% by weight and more preferably still from 0.1 to 6% by weight, with respect to the total weight of the composition.

The merocyanine dicyano or cyanoacetate derivatives in accordance with the present invention are chosen from the group consisting of:

(i) those corresponding to the following general formula (I):

$$\left[ \begin{array}{c} R_1 \\ R_2 \end{array} N \diagup\diagdown \diagup\diagdown \begin{array}{c} A \\ \diagdown N \end{array} \right]_n \quad (I)$$

in which:
A is the —C≡N or —(C═O)OR$_3$ group,
R$_1$ and R$_2$, which are identical or different, denote a linear or branched C$_1$-C$_3$ alkyl radical, the hydroxyethyl group or a C$_5$-C$_6$ cycloalkyl,
R$_3$ denotes a linear or branched C$_1$-C$_8$ alkyl radical,
n is 1 or 2;
with the proviso that, when n=2, R$_1$, R$_2$ or R$_3$ is a C$_2$-C$_{16}$ alkyl diradical or else R$_1$ and R$_2$ form, with 2 nitrogen atoms, a cyclic divalent —(CH$_2$)$_m$— radical with m being an integer ranging from 3 to 7;

(ii) the compound (a):

RN = 1015037-82-7

(iii) the compound (b):

RN = 193292-32-9

(iv) the compound (c):

RN = 105596-16-5

(v) the compound (l):

(vi) the compound (p):

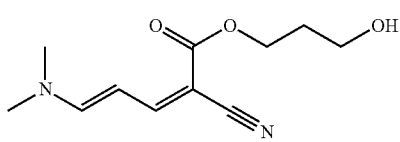

(vii) the compound (v):

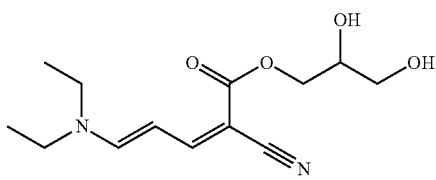

(viii) the compound (w):

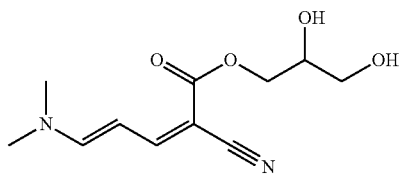

(ix) the compound (x):

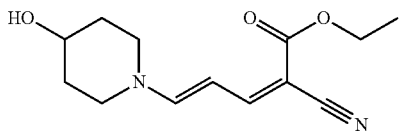

(x) the compound (aa)

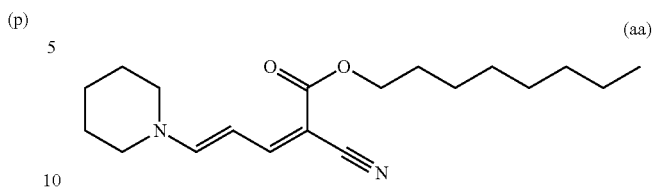

(xi) the compound (bb)

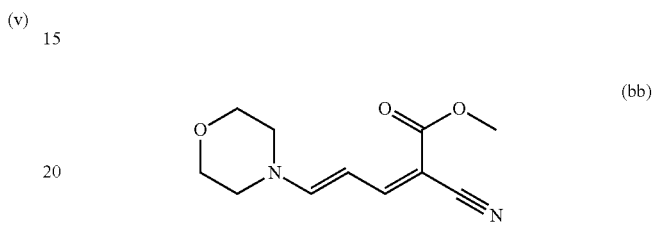

RN = 467465-33-4

The compounds of formula (I) and the compounds (a), (b), (c), (l), (p), (v), (w), (x), (aa) and (bb) can be in the E,E-, E,Z- or Z,Z-geometrical isomeric forms.

When n=2, "diradical" is understood to mean a divalent radical so that the two units

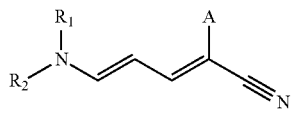

are bonded to one another via this diradical.

Mention may be made, by way of illustration, of the following compounds q and r:

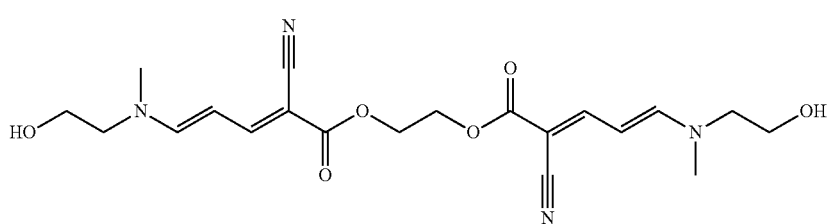

RN = 647829-03-6

In the case where n=2, mention may be made, as example of cyclic divalent —(CH$_2$)$_m$— radical formed by R$_1$ and R$_2$ with the 2 nitrogen atoms, of that of the compound (hh):

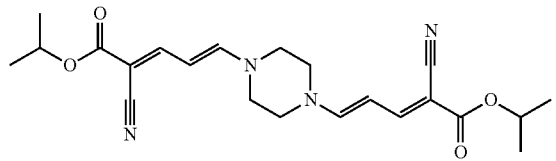
(hh)

Mention may be made, as linear or branched C$_1$-C$_3$ alkyl radicals, for example, of methyl, ethyl, n-propyl, 1-methylethyl or isopropyl.

Mention may be made, as linear or branched C$_1$-C$_8$ alkyl radicals, for example, of methyl, ethyl, n-propyl, 1-methylethyl, isopropyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,2,2-trimethylpropyl, 1-ethyl-1-methylpropyl, 1-ethyl-2-methylpropyl, n-heptyl or n-octyl.

Mention may be made, as C$_5$-C$_6$ cycloalkyl radicals, of cyclopentyl or cyclohexyl.

Mention may be made, among the compounds of formula (I), of those of the following formulae (d), (e), (f), (g), (h), (i), (j), (k), (m), (n), (o), (q), (r), (s), (t), (u), (y), (z), (cc), (ee), (ff), (gg) and (hh) or their E,E-, E,Z- or Z,Z-isomers:

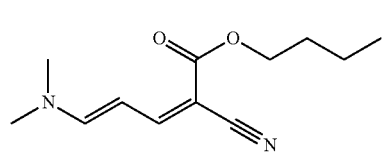
(d)
RN = 256444-59-4

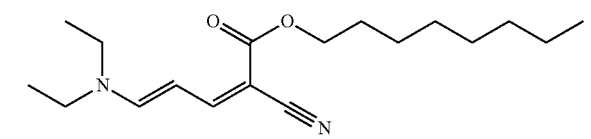
(e)

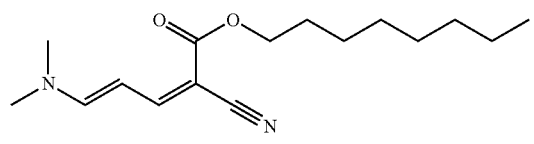
(f)

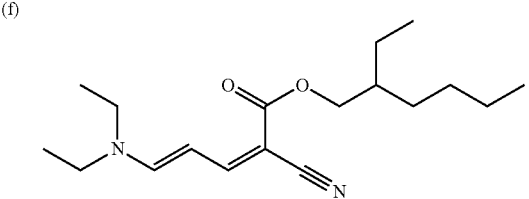
(g)
RN = 647829-00-3

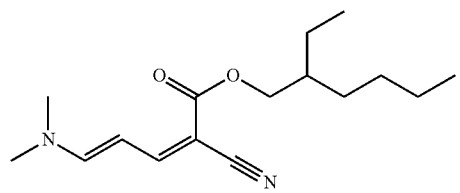
(h)
RN = 256444-60-7

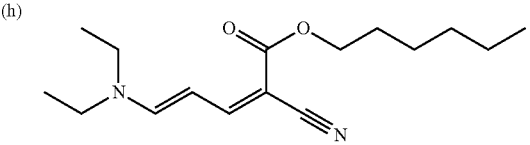
(i)

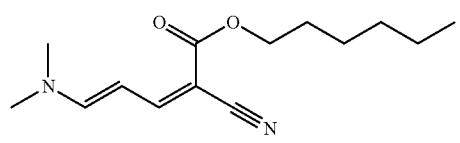
(j)

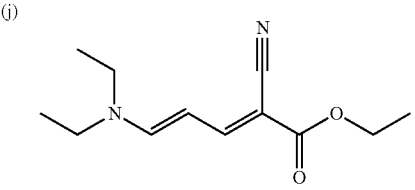
(k)
RN = 1015037-96-3

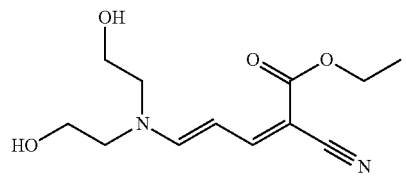
(m)

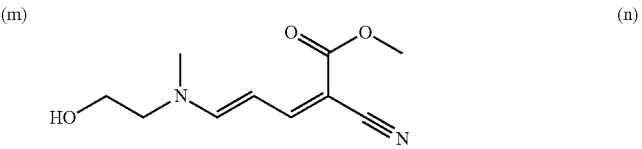
(n)
RN = 105744-06-7

-continued
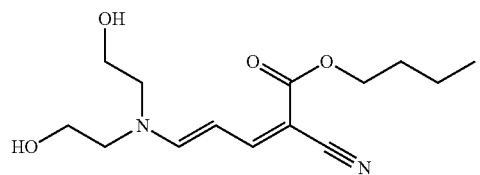
(o)
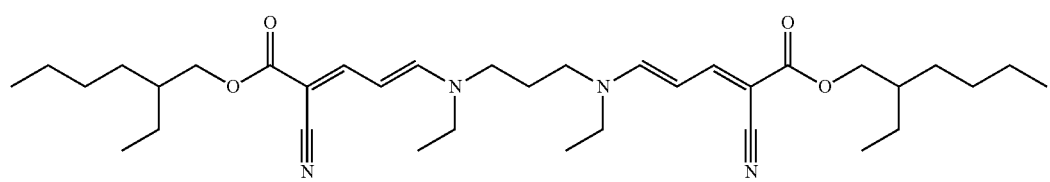
(q)
RN = 647829-03-6
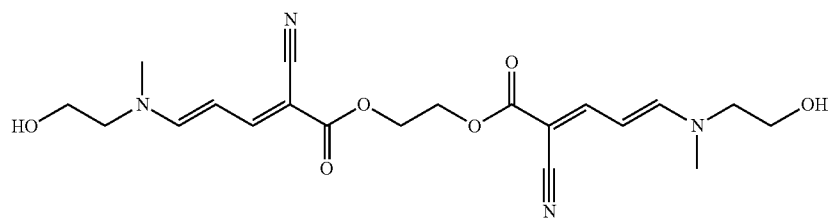
(r)
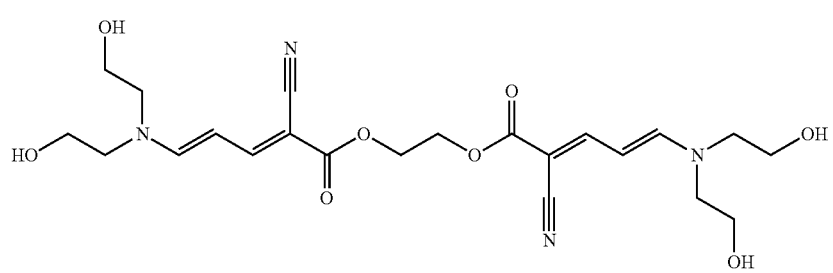
(s)
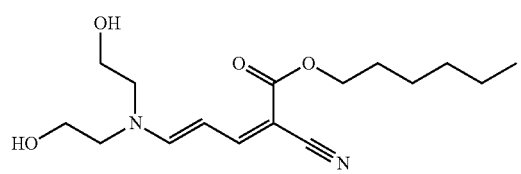
(t)
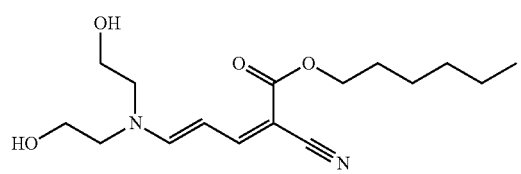
(u)
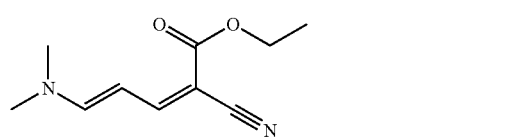
(y)
RN = 51513-16-7
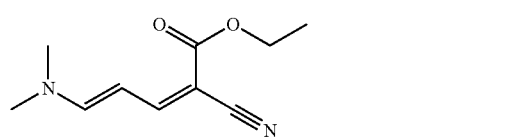
(z)
RN = 26932-70-7
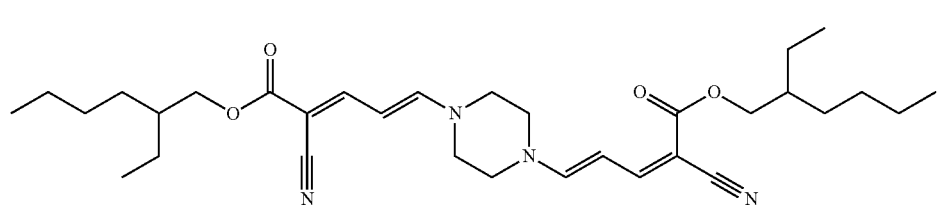
(cc)
RN = 647829-05-8

-continued
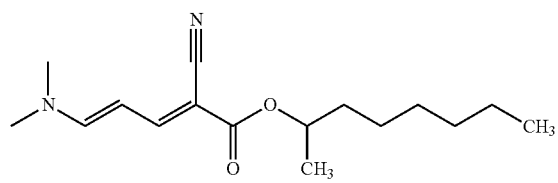
(ee)
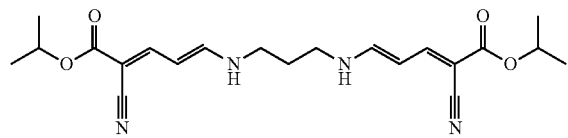
(ff)
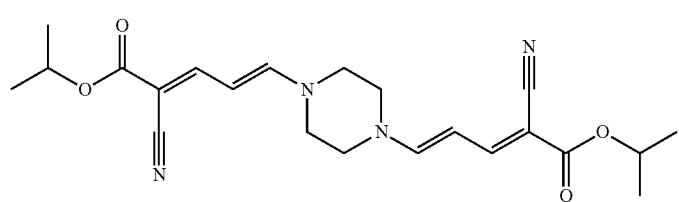
(gg)
(hh)
Preference will even more particularly be given, among the merocyanine derivatives in accordance with the present invention, to the following to compounds or their E,E-, E,Z- or Z,Z-isomers:
-continued
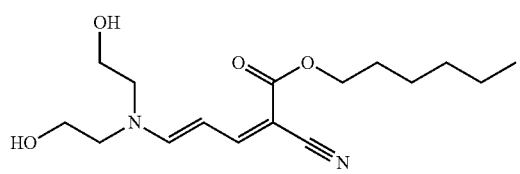
(t)
(u)
(e)
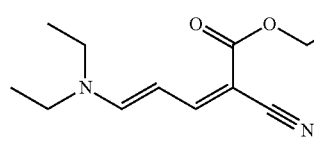
(f)
(aa)
(g)
(ee)
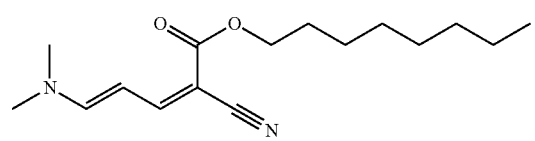
(gg)
(h)
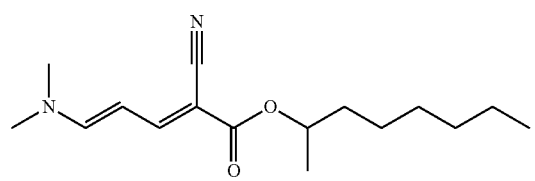
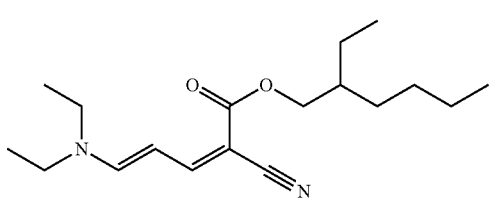
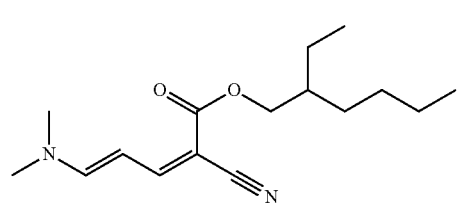
The merocyanine derivatives in accordance with the invention, in particular those of formula (I), can be prepared according to a method described in U.S. Pat. No. 4,045,229 and U.S. Pat. No. 4,195,999, according to the following scheme (Route 1):

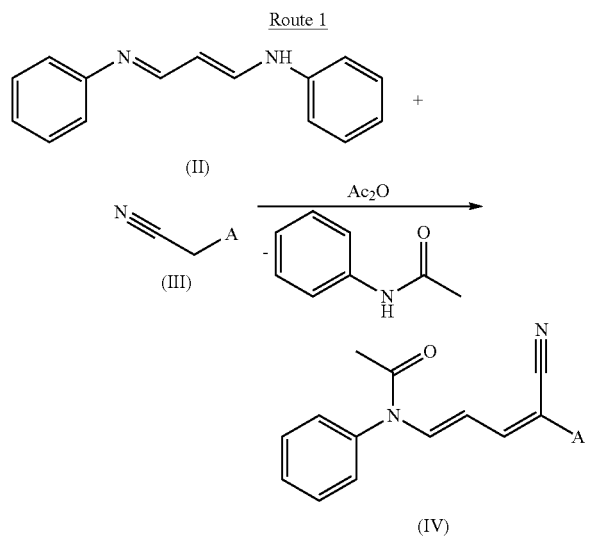

in which the $R_1$, $R_2$ and A radicals have the same meanings as in the formula (I).

The merocyanine derivatives in accordance with the invention, in particular those of formula (I), can be prepared according to a method described in Patent WO 0020388, according to the following scheme (Route 2):

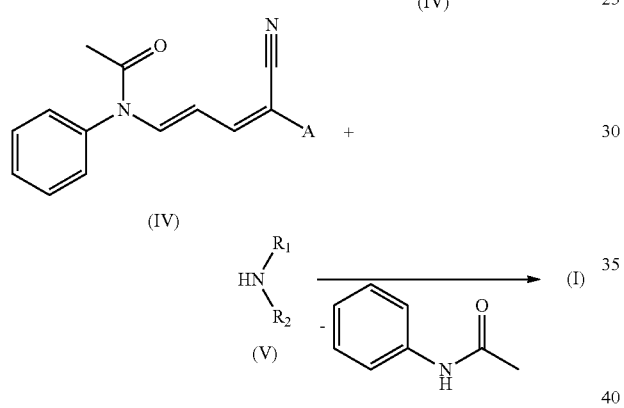

in which the $R_1$, $R_2$ and A radicals have the same meanings as in the formula (I).

The merocyanine derivatives in accordance with the invention, in particular those of formula (I) in which A represents —(C═O)$OR_3$ and $R_3$ denotes an alkyl having at least 3 carbon atoms, can be obtained by transesterification according to the scheme below, which route is described in Patent US 2008076940 and can use, inter alia, as catalyst, titanium(IV) isopropoxide (Route 3):

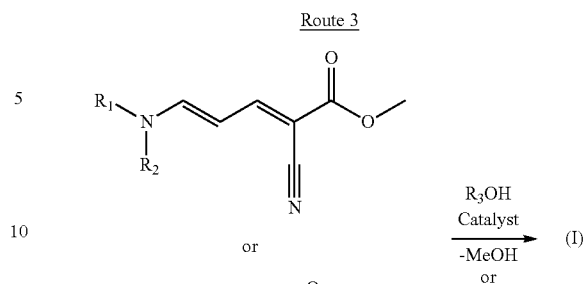

The merocyanine derivatives in accordance with the invention, in particular those of formula (I) in which $R_1$ and $R_2$ denote an alkyl having at least 3 carbon atoms, can be obtained by transamination, according to the scheme below (Route 4):

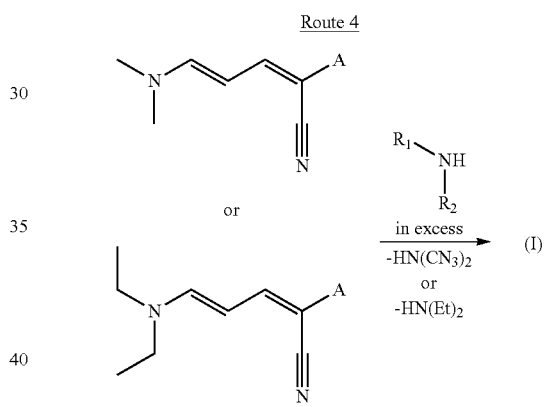

Among the merocyanine compounds in accordance with the invention, some are novel.

Mention may be made, among these novel compounds, of those corresponding to the following formula (VI):

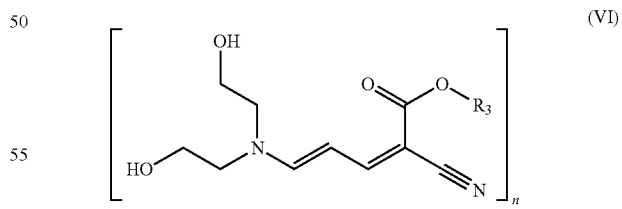

in which $R_3$ and n have the same meanings as in the formula (I), and their E,E-, to E,Z- or Z,Z-isomeric forms.

Mention may be made, as examples of compounds of formula (VI), of the compounds (m), (o), (s), (t) and (u), and also their E,E-, E,Z- or Z,Z-isomeric forms.

Mention may also be made, among these novel compounds, of the compounds (e), (f), (i), (j), (l), (p), (r), (v), (w), (x), (aa), (ee), (ff), (gg) and (hh), and also their E,E-, E,Z- or Z,Z-isomeric forms.

The hydrophilic or water-soluble merocyanine screening agent or agents in accordance with the invention can be present in the compositions according to the invention at a concentration of between 0.1 and 10% by weight, preferably between 0.2 and 5% by weight, with respect to the total weight of the composition.

The compositions in accordance with the invention can additionally comprise other additional organic or inorganic UV screening agents which are active in the UV-A and/or UV-B regions and which are water-soluble or fat-soluble or else insoluble in the cosmetic solvents commonly used.

Of course, a person skilled in the art will take care to choose the optional additional screening agent or agents and/or their amounts so that the advantageous properties intrinsically attached to the compositions in accordance with the invention are not, or not substantially, detrimentally affected by the envisaged addition or additions, in particular the improvement in the photostability of the dibenzoylmethane derivative.

The additional organic screening agents are chosen in particular from anthranilics; cinnamic derivatives; salicylic derivatives; benzylidenecamphor derivatives; benzophenone derivatives; β,β-diphenylacrylate derivatives; triazine derivatives; phenylbenzotriazole derivatives; benzalmalonate derivatives, in particular those cited in U.S. Pat. No. 5,624,663; phenylbenzimidazole derivatives; imidazolines; bisbenzazolyl derivatives, such as described in EP 669 323 and U.S. Pat. No. 2,463,264; p-aminobenzoic acid (PABA) derivatives; methylenebis(hydroxyphenylbenzotriazole) derivatives, such as described in U.S. Pat. No. 5,237,071, U.S. Pat. No. 5,166,355, GB 2 303 549, DE 197 26 184 and EP 893 119; benzoxazole derivatives, such as described in Patent Applications EP 0 832 642, EP 1 027 883, EP 1 300 137 and DE 10162844; screening polymers and screening silicones, such as those described in particular in Application WO 93/04665; dimers derived from α-alkylstyrene, such as those described in Patent Application DE 19855649; 4,4-diarylbutadienes, such as described in Applications EP 0 967 200, DE 19746654, DE 19755649, EP-A-1 008 586, EP 1 133 980 and EP 133 981; merocyanine derivatives other than those of formula (I), (a), (b), (c), (l), (p), (v), (w), (x), (aa) or (bb), such as those described in Applications WO 04006878, WO 05058269 and WO 06032741; and their mixtures.

Mention may be made, as examples of organic UV screening agents, of those denoted below under their INCI names:
para-Aminobenzoic Acid Derivatives:
PABA,
Ethyl PABA,
Ethyl Dihydroxypropyl PABA,
Ethylhexyl Dimethyl PABA, sold in particular under the name "Escalol 507" by ISP,
Glyceryl PABA,
PEG-25 PABA, sold under the name "Uvinul P25" by BASF,
Salicylic Derivatives:
Homosalate, sold under the name "Eusolex HMS" by Rona/EM Industries,
Ethylhexyl Salicylate, sold under the name "Neo Heliopan OS" by Symrise,
Dipropyleneglycol Salicylate, sold under the name "Dipsal" by Scher,
TEA Salicylate, sold under the name "Neo Heliopan TS" by Symrise,
Cinnamic Derivatives:
Ethylhexyl Methoxycinnamate, sold in particular under the trade name "Parsol MCX" by DSM Nutritional Products,
Isopropyl Methoxycinnamate,
Isoamyl Methoxycinnamate, sold under the trade name "Neo Heliopan E 1000" by Symrise,
Cinoxate,
DEA Methoxycinnamate,
Diisopropyl Methylcinnamate,
Glyceryl Ethylhexanoate Dimethoxycinnamate,
β,β-Diphenylacrylate Derivatives:
Octocrylene, sold in particular under the trade name "Uvinul N539" by BASF,
Etocrylene, sold in particular under the trade name "Uvinul N35" by BASF,
Benzophenone Derivatives:
Benzophenone-1, sold under the trade name "Uvinul 400" by BASF,
Benzophenone-2, sold under the trade name "Uvinul D50" by BASF,
Benzophenone-3 or Oxybenzone, sold under the trade name "Uvinul M40" by BASF,
Benzophenone-4, sold under the trade name "Uvinul MS40" by BASF,
Benzophenone-5,
Benzophenone-6, sold under the trade name "Helisorb 11" by Norquay,
Benzophenone-8, sold under the trade name "Spectra-Sorb UV-24" by American Cyanamid,
Benzophenone-9, sold under the trade name "Uvinul DS-49" by BASF,
Benzophenone-12,
n-Hexyl 2-(4-diethylamino-2-hydroxybenzoyl)benzoate, sold under the trade name "Uvinul A+" or in the form of a mixture with octyl methoxycinnamate under the trade name "Uvinul A+B" by BASF,
1,1'-(1,4-piperazinediyl)bis[1-[2-[4-(diethylamino)-2-hydroxybenzoyl]phenyl]-methanone] (CAS 919803-06-8),
Benzylidenecamphor Derivatives:
3-Benzylidene camphor, manufactured under the name "Mexoryl SD" by Chimex,
4-Methylbenzylidene camphor, sold under the name "Eusolex 6300" by Merck,
Benzylidene Camphor Sulfonic Acid, manufactured under the name "Mexoryl SL" by Chimex,
Camphor Benzalkonium Methosulfate, manufactured under the name "Mexoryl SO" by Chimex,
Terephthalylidene Dicamphor Sulfonic Acid, manufactured under the name "Mexoryl SX" by Chimex,
Polyacrylamidomethyl Benzylidene Camphor, manufactured under the name "Mexoryl SW" by Chimex,
Phenylbenzimidazole Derivatives:
Phenylbenzimidazole Sulfonic Acid, sold in particular under the trade name "Eusolex 232" by Merck,
Disodium Phenyl Dibenzimidazole Tetrasulfonate, sold under the trade name "Neo Heliopan AP" by Symrise,
Phenylbenzotriazole Derivatives:
Drometrizole Trisiloxane, sold under the name "Silatrizole" by Rhodia Chimie,
Methylene Bis-Benzotriazolyl Tetramethylbutylphenol, sold in the solid form under the trade name "Mixxim BB/100" by Fairmount Chemical or in the micronized form in aqueous dispersion under the trade name "Tinosorb M" by Ciba Specialty Chemicals,
Triazine Derivatives:
Bis-Ethylhexyloxyphenol Methoxyphenyl Triazine, sold under the trade name "Tinosorb S" by Ciba-Geigy,
Ethylhexyl Triazone, sold in particular under the trade name "Uvinul T150" by BASF,
Diethylhexyl Butamido Triazone, sold under the trade name "Uvasorb HEB" by Sigma 3V, 2,4,6-Tris(diisobutyl 4'-aminobenzalmalonate)-s-triazine,
2,4,6-Tris(dineopentyl 4'-aminobenzalmalonate)-s-triazine,
2,4-Bis(dineopentyl 4'-aminobenzalmalonate)-6-(n-butyl 4'-aminobenzoate)-s-triazine,
2,4-Bis(n-butyl 4'-aminobenzoate)-6-[(3-{1,3,3,3-tetramethyl-1-[(trimethylsilyl)-oxy]disiloxanyl}propyl)amino]-s-triazine, The symmetrical triazine screening agents described in U.S. Pat. No. 6,225,467, Application WO 2004/085412 (see compounds 6 and 9) or the document "Symmetrical Triazine Derivatives", IP.COM Journal, IP.COM INC, WEST HENRIETTA, NY, US (20 Sep. 2004), in particular the 2,4,6-tris(biphenyl)-1,3,5-triazines (especially 2,4,6-tris(biphenyl-4-yl)-1,3,5-triazine) and 2,4,6-tris(terphenyl)-1,3,5-triazine, which is taken up again in the Beiersdorf applications WO 06/035000, WO 06/034982, WO 06/034991, WO 06/035007, WO 2006/034992 and WO 2006/034985.

Anthranilic Derivatives:
Menthyl anthranilate, sold under the trade name "Neo Heliopan MA" by Symrise, Imidazoline Derivatives:
Ethylhexyl Dimethoxybenzylidene Dioxoimidazoline Propionate, Benzalmalonate Derivatives:
Dineopentyl 4'-methoxybenzalmalonate,
Polyorganosiloxane comprising benzalmalonate functional groups, such as Polysilicone-15, sold under the trade name "Parsol SLX" by Hoffmann-LaRoche, 4,4-Diarylbutadiene Derivatives:
1,1-Dicarboxy(2,2'-dimethylpropyl)-4,4-diphenylbutadiene, Benzoxazole Derivatives:
2,4-bis[5-1(dimethylpropyl)benzoxazol-2-yl-(4-phenyl) imino]-6-(2-ethylhexyl)imino-1,3,5-triazine, sold under the name of Uvasorb K2A by Sigma 3V,
and their mixtures.

The preferred additional organic screening agents are chosen from:
Ethylhexyl Methoxycinnamate,
Homosalate,
Ethylhexyl Salicylate,
Octocrylene,
Phenylbenzimidazole Sulfonic Acid,
Benzophenone-3,
Benzophenone-4,
Benzophenone-5,
n-Hexyl 2-(4-diethylamino-2-hydroxybenzoyl)benzoate,
1,1'-(1,4-piperazinediyl)bis[1-[2-[4-(diethylamino)-2-hydroxybenzoyl]phenyl]-methanone]
4-Methylbenzylidene Camphor,
Terephthalylidene Dicamphor Sulfonic Acid,
Disodium Phenyl Dibenzimidazole Tetrasulfonate,
Ethylhexyl Triazone,
Bis-Ethylhexyloxyphenol Methoxyphenyl Triazine,
Diethylhexyl Butamido Triazone,
2,4,6-Tris(biphenyl-4-yl)-1,3,5-triazine,
2,4,6-Tris(dineopentyl 4'-aminobenzalmalonate)-s-triazine,
2,4,6-Tris-(diisobutyl 4'-aminobenzalmalonate)-s-triazine,
2,4-Bis(dineopentyl 4'-aminobenzalmalonate)-6-(n-butyl 4'-aminobenzoate)-s-triazine,
2,4-Bis(n-butyl 4'-aminobenzoate)-6-[(3-{1,3,3,3-tetramethyl-1-[(trimethylsilyl)-oxy]disiloxanyl}propyl)amino]-s-triazine,
Methylene Bis-Benzotriazolyl Tetramethylbutylphenol,
Drometrizole Trisiloxane, Polysilicone-15,
Dineopentyl 4'-methoxybenzalmalonate,
1,1-Dicarboxy(2,2'-dimethylpropyl)-4,4-diphenylbutadiene,
2,4-Bis[5-1(dimethylpropyl)benzoxazol-2-yl-(4-phenyl) imino]-6-(2-ethylhexyl)imino-1,3,5-triazine,
and their mixtures.

The additional inorganic screening agents are chosen from coated or uncoated metal oxide pigments, such as, for example, pigments formed of titanium oxide (amorphous or crystalline in the rutile and/or anatase form), iron oxide, zinc oxide, zirconium oxide or cerium oxide, which are all UV photoprotective agents well known per se.

The pigments may or may not be coated.

The coated pigments are pigments which have been subjected to one or more surface treatments of chemical, electronic, mechanochemical and/or mechanical nature with compounds such as described, for example, in Cosmetics & Toiletries, February 1990, Vol. 105, pp. 53-64, such as amino acids, beeswax, fatty acids, fatty alcohols, anionic surfactants, lecithins, sodium, potassium, zinc, iron or aluminium salts of fatty acids, metal alkoxides (titanium or aluminium alkoxides), polyethylene, silicones, proteins (collagen, elastin), alkanolamines, silicon oxides, metal oxides or sodium hexametaphosphate.

In a known way, the silicones are organosilicon polymers or oligomers comprising a linear or cyclic and branched or crosslinked structure, of variable molecular weight, obtained by polymerization and/or polycondensation of suitably functionalized silanes and essentially composed of a repetition of main units in which the silicon atoms are connected to one another via oxygen atoms (siloxane bond), optionally substituted hydrocarbon radicals being connected to directly to the said silicon atoms via a carbon atom.

The term "silicones" also encompasses the silanes necessary for their preparation, in particular alkylsilanes.

The silicones used for the coating of the pigments suitable for the present invention are preferably chosen from the group consisting of alkylsilanes, polydialkylsiloxanes and polyalkylhydrosiloxanes. More preferably still, the silicones are chosen from the group consisting of octyltrimethylsilane, polydimethylsiloxanes and polymethylhydrosiloxanes.

Of course, the pigments formed of metal oxides may, before their treatment with silicones, have been treated with other surfacing agents, in particular with cerium oxide, alumina, silica, aluminium compounds, silicon compounds or their mixtures.

The coated pigments are, for example, titanium oxides coated:
  with silica, such as the product "Sunveil" from Ikeda and the product "Eusolex T-AVO" from Merck
  with silica and with iron oxide, such as the product "Sunveil F" from Ikeda,
  with silica and with alumina, such as the products "Microtitanium Dioxide MT 500 SA" and "Microtitanium Dioxide MT 100 SA" from Tayca, "Tioveil" from Tioxide and "Mirasun TiW 60" from Rhodia,
  with alumina, such as the products "Tipaque TTO-55 (B)" and "Tipaque TTO-55 (A)" from Ishihara and "UVT 14/4" from Kemira,
  with alumina and with aluminium stearate, such as the product "Microtitanium Dioxide MT 100 TV", "MT 100 TX", "MT 100 Z" or "MT-01" from Tayca and the products "Solaveil CT-10 W", "Solaveil CT 100" and "Solaveil CT 200" from Uniqema,
  with silica, with alumina and with alginic acid, such as the product "MT-100 AQ" from Tayca,
  with alumina and with aluminium laurate, such as the product "Microtitanium Dioxide MT 100 S" from Tayca, with iron oxide and with iron stearate, such as the product "Microtitanium Dioxide MT 100 F" from Tayca,
with zinc oxide and with zinc stearate, such as the product "BR351" from Tayca,
with silica and with alumina and treated with a silicone, such as the products "Microtitanium Dioxide MT 600 SAS", "Microtitanium Dioxide MT 500 SAS" or "Microtitanium Dioxide MT 100 SAS" from Tayca,
with silica, with alumina and with aluminium stearate and treated with a silicone, such as the product "STT-30-DS" from Titan Kogyo,
with silica and treated with a silicone, such as the product "UV-Titan X 195" from Kemira or the product SMT-100 WRS from Tayca,
with alumina and treated with a silicone, such as the products "Tipaque TTO-55 (S)" from Ishihara or "UV Titan M 262" from Kemira,
with triethanolamine, such as the product "STT-65-S" from Titan Kogyo,
with stearic acid, such as the product "Tipaque TTO-55 (C)" from Ishihara,
with sodium hexametaphosphate, such as the product "Microtitanium Dioxide MT 150 W" from Tayca.

Other titanium oxide pigments treated with a silicone are, for example, $TiO_2$ treated with octyltrimethylsilane, such as that sold under the trade name "T 805" by Degussa Silices, $TiO_2$ treated with a polydimethylsiloxane, such as that sold under the trade name "70250 Cardre UF TiO2Sl3" by Cardre, or anatase/rutile $TiO_2$ treated with a polydimethylhydrosiloxane, such as that sold under the trade name "Microtitanium Dioxide USP Grade Hydrophobic" by Color Techniques.

The uncoated titanium oxide pigments are, for example, sold by Tayca under the trade names "Microtitanium Dioxide MT 500 B" or "Microtitanium Dioxide MT600 B", by Degussa under the name "P 25", by Wacker under the name "Oxyde de titane transparent PW", by Miyoshi Kasei under the name "UFTR", by Tomen under the name "ITS" and by Tioxide under the name "Tioveil AQ".

The uncoated zinc oxide pigments are, for example:
those sold under the name "Z-cote" by Sunsmart;
those sold under the name "Nanox" by Elementis;
those sold under the name "Nanogard WCD 2025" by Nanophase Technologies.

The coated zinc oxide pigments are, for example:
those sold under the name "Z-cote HP1" by Sunsmart (ZnO coated with dimethicone);
those sold under the name "Oxide zinc CS-5" by Toshibi (ZnO coated with polymethylhydrosiloxane);
those sold under the name "Nanogard Zinc Oxide FN" by Nanophase Technologies (as a 40% dispersion in Finsolv TN, $C_{12}$-$C_{15}$ alkyl benzoate);
those sold under the name "Daitopersion Zn-30" and "Daitopersion Zn-50" by Daito (dispersions in oxyethylenated polydimethylsiloxane/cyclo-polymethylsiloxane comprising 30% or 50% of zinc oxides coated with silica and polymethylhydrosiloxane);
those sold under the name "NFD Ultrafine ZnO" by Daikin (ZnO coated with phosphate of perfluoroalkyl and copolymer based on perfluoroalkylethyl as a dispersion in cyclopentasiloxane);
those sold under the name "SPD-Z1" by Shin-Etsu (ZnO coated with silicone-grafted acrylic polymer dispersed in cyclodimethylsiloxane);
those sold under the name "Escalol Z100" by ISP (alumina-treated ZnO dispersed in the ethylhexyl methoxycinnamate/PVP-hexadecene copolymer/methicone mixture);
those sold under the name "Fuji ZnO-SMS-10" by Fuji Pigment (ZnO coated with silica and polymethylsilsesquioxane);
those sold under the name "Nanox Gel TN" by Elementis (ZnO dispersed at 55% in $C_{12}$-$C_{15}$ alkyl benzoate with hydroxystearic acid polycondensate).

The uncoated cerium oxide pigments are sold, for example, under the name "Colloidal Cerium Oxide" by Rhône-Poulenc.

The uncoated iron oxide pigments are, for example, sold by Arnaud under the names "Nanogard WCD 2002 (FE 45B)", "Nanogard Iron FE 45 BL AQ", "Nanogard FE 45R AQ" or "Nanogard WCD 2006 (FE 45R)", or by Mitsubishi under the name "TY-220".

The coated iron oxide pigments are, for example, sold by Arnaud under the names "Nanogard WCD 2008 (FE 45B FN)", "Nanogard WCD 2009 (FE 45B 556)", "Nanogard FE 45 BL 345" or "Nanogard FE 45 BL", or by BASF under the name "Oxyde de fer transparent".

Mention may also be made of mixtures of metal oxides, in particular of titanium dioxide and of cerium dioxide, including the mixture of equal weights of titanium dioxide coated with silica and of cerium dioxide coated with silica sold by Ikeda under the name "Sunveil A", and also the mixture of titanium dioxide and of zinc dioxide coated with alumina, with silica and with silicone, such as the product "M 261" sold by Kemira, or coated with alumina, with silica and with glycerol, such as the product "M 211" sold by Kemira.

The additional UV screening agents are generally present in the compositions according to the invention in proportions ranging from 0.01 to 20% by weight, with respect to the total weight of the composition, and preferably ranging from 0.1 to 10% by weight, with respect to the total weight of the composition.

The compositions in accordance with the present invention can additionally comprise conventional cosmetic adjuvants chosen in particular from oils, waxes, organic solvents, ionic or nonionic and hydrophilic or lipophilic thickeners, softening agents, humectants, opacifiers, stabilizing agents, emollients, silicones, antifoaming agents, fragrances, preservatives, anionic, cationic, nonionic, zwitterionic or amphoteric surfactants, active principles, fillers, polymers, propellants, basifying or acidifying agents or any other ingredient commonly used in the cosmetics and/or dermatological field.

Mention may be made, as oils, for example, of mineral oils (liquid paraffin); vegetable oils (sweet almond, macadamia, blackcurrant seed or jojoba oil); synthetic oils, such as perhydrosqualene, fatty alcohols, fatty amides (such as isopropyl lauroyl sarcosinate, sold under the name of "Eldew SL-205" by Ajinomoto), fatty acids or esters, such as $C_{12}$-$C_{15}$ alkyl benzoate, sold under the trade name "Finsolv TN" or "Witconol TN" by Witco, 2-ethylphenyl benzoate, such as the commercial product sold under the name X-Tend 226® by ISP, octyl palmitate, isopropyl lanolate, triglycerides, including those of capric/caprylic acids, dicaprylyl carbonate, sold under the name "Cetiol CC" by Cognis, or oxyethylenated or oxypropylenated fatty esters and ethers; silicone oils (cyclomethicone, polydimethylsiloxanes or PDMSs); fluorinated oils; polyalkylenes; or trialkyl trimellitates, such as tridecyl trimellitate.

Mention may be made, as wax, for example, of carnauba wax, beeswax, hydrogenated castor oil, polyethylene waxes and polymethylene waxes, such as that sold under the name Cirebelle 303 by Sasol.

Mention may be made, among organic solvents, for example, of lower alcohols and polyols. The latter can be chosen from glycols and glycol ethers, such as ethylene glycol, propylene glycol, butylene glycol, dipropylene glycol or diethylene glycol.

Mention may be made, as hydrophilic thickeners, for example, of carboxyvinyl polymers, such as the Carbopols (Carbomers) and the Pemulens (acrylate/$C_{10}$-$C_{30}$ alkyl acrylate copolymer); polyacrylamides, such as, for example, the crosslinked copolymers sold under the names Sepigel 305 (CTFA name: polyacrylamide/C13-14 isoparaffin/Laureth 7) or Simulgel 600 (CTFA name: acrylamide/sodium acryloyldimethyltaurate copolymer/isohexadecane/polysorbate 80) by Seppic; optionally crosslinked and/or neutralized polymers and copolymers of 2-acrylamido-2-methylpropanesulphonic acid, such as the poly(2-acrylamido-2-methylpropanesulphonic acid) sold by Hoechst under the trade name "Hostacerin AMPS" (CTFA name: ammonium polyacryloyldimethyl taurate) or Simulgel 800, sold by Seppic (CTFA name: sodium polyacryloyldimethyl taurate/polysorbate 80/sorbitan oleate); copolymers of 2-acrylamido-2-methylpropanesulphonic acid and of hydroxyethyl acrylate, such as Simulgel NS and Sepinov EMT 10, sold by Seppic; cellulose derivatives, such as hydroxyethylcellulose; polysaccharides and in particular gums, such as xanthan gum; water-soluble or water-dispersible silicone derivatives, such as acrylic silicones, silicone polyethers and cationic silicones; and their mixtures.

Mention may be made, as lipophilic thickeners, for example, of synthetic polymers, such as the poly($C_{10}$-$C_{30}$ alkyl acrylates) sold under the names "Intelimer IPA 13-1" and "Intelimer IPA 13-6" by Landec, or of modified clays, such as hectorite and its derivatives, such as the products sold under the Bentone names.

Of course, a person skilled in the art will take care to choose the optional additional compound or compounds mentioned above and/or their amounts so that the advantageous properties intrinsically attached to the compositions in accordance with the invention are not, or not substantially, detrimentally affected by the envisaged addition or additions, in particular the improvement in the photostability of the dibenzoylmethane derivative.

The compositions according to the invention can be prepared according to techniques well known to a person skilled in the art. They can be provided in particular in the form of a simple or complex (O/W, W/O, O/W/O or W/O/W) emulsion, such as a cream, a milk or a cream gel; in the form of an aqueous gel; or in the form of a lotion. They can optionally be packaged as an aerosol and be provided in the foam or spray form.

Preferably, the compositions according to the invention are provided in the form of an oil-in-water or water-in-oil emulsion.

The emulsification processes which can be used are of the paddle or propeller, rotor-stator and HPH type.

It is also possible, by HPH (between 50 and 800 bar), to obtain stable dispersions with drop sizes which may be as low as 100 nm.

The emulsions generally comprise at least one emulsifying surfactant chosen from amphoteric, anionic, cationic or nonionic emulsifying surfactants, used alone or as a mixture. The emulsifiers are appropriately chosen according to the emulsion to be obtained (W/O or O/W emulsion).

Mention may be made, as emulsifying surfactants which can be used for the preparation of the W/O emulsions, for example, of alkyl esters or ethers of sorbitan, of glycerol or of sugars; or silicone surfactants, such as dimethicone copolyols, for example the mixture of cyclomethicone and of dimethicone copolyol sold under the name "DC 5225 C" by Dow Corning, and alkyl dimethicone copolyols, such as lauryl methicone copolyol, sold under the name "Dow Corning 5200 Formulation Aid" by Dow Corning, or cetyl dimethicone copolyol, such as the product sold under the name Abil EM 90R by Goldschmidt and the mixture of cetyl dimethicone copolyol, of polyglycerol (4 mol) isostearate and of hexyl laurate sold under the name Abil WE O9 by Goldschmidt. It is also possible to add thereto one or more coemulsifiers which, advantageously, can be chosen from the group consisting of polyol alkyl esters.

Mention may in particular be made, as polyol alkyl esters, of polyethylene glycol esters, such as PEG-30 dipolyhydroxystearate, such as the product sold under the name Arlacel P135 by ICI.

Mention may be made, as glycerol and/or sorbitan esters, for example, of polyglycerol isostearate, such as the product sold under the name Isolan GI 34 by Goldschmidt; sorbitan isostearate, such as the product sold under the name Arlacel 987 by ICI; sorbitan glyceryl isostearate, such as the product sold under the name Arlacel 986 by ICI, and their mixtures.

Mention may be made, for the O/W emulsions, for example, as emulsifying surfactants, of nonionic emulsifiers, such as oxyalkylenated (more particularly polyoxyethylenated) esters of fatty acids and of glycerol; oxyalkylenated esters of fatty acids and of sorbitan; oxyalkylenated (oxyethylenated and/or oxypropylenated) esters of fatty acids, such as the PEG-100 stearate/glyceryl stearate mixture sold, for example, by ICI under the name Arlacel 165; oxyalkylenated (oxyethylenated and/or oxypropylenated) ethers of fatty alcohols; esters of sugars, such as sucrose stearate; or ethers of fatty alcohol and of sugar, in particular alkyl polyglucosides (APGs), such as decyl glucoside and lauryl glucoside, sold, for example, by Henkel under the respective names Plantaren 2000 and Plantaren 1200, cetearyl glucoside, optionally as a mixture with cetearyl alcohol, sold, for example, under the name Montanov 68 by Seppic, under the name Tegocare CG90 by Goldschmidt and under the name Emulgade KE3302 by Henkel, and arachidyl glucoside, for example in the form of the mixture of arachidyl and behenyl alcohols and of arachidyl glucoside sold under the name Montanov 202 by Seppic. According to a specific embodiment of the invention, the mixture of the alkyl polyglucoside as defined above with the corresponding fatty alcohol can be in the form of a self-emulsifying composition, for example as described in the document WO-A-92/06778.

When an emulsion is involved, the aqueous phase of the latter can comprise a nonionic vesicular dispersion prepared according to known processes (Bangham, Standish and Watkins, J. Mol. Biol., 13, 238 (1965), FR 2 315 991 and FR 2 416 008).

The compositions according to the invention have applications in a large number of treatments, in particular cosmetic treatments, of the skin, lips and hair, including the scalp, in particular for protecting and/or caring for the skin, lips and/or hair and/or for making up the skin and/or lips.

Another subject-matter of the present invention is composed of the use of the compositions according to the invention as defined above in the manufacture of products for the cosmetic treatment of the skin, lips, nails, hair, eyelashes, eyebrows and/or scalp, in particular of care products, sun protection products and make-up products.

The cosmetic compositions according to the invention can, for example, be used as make-up product.

The cosmetic compositions according to the invention can, for example, be used as care product and/or sun protection product for the face and/or body with a liquid to semi-liquid consistency, such as milks, relatively smooth creams, cream gels or pastes. They can optionally be packaged as an aerosol and be provided in the form of a foam or of a spray.

The compositions according to the invention in the form of vaporizable fluid lotions in accordance with the invention are applied to the skin or hair in the form of fine particles by means of pressurizing devices. The devices in accordance with the invention are well known to a person skilled in the art and comprise nonaerosol pumps or "atomizers", aerosol containers comprising a propellant and aerosol pumps using compressed air as propellant. The latter are described in U.S. Pat. No. 4,077,441 and U.S. Pat. No. 4,850,517 (forming an integral part of the content of the description).

The compositions packaged as an aerosol in accordance with the invention generally comprise conventional propellants, such as, for example, hydrofluorinated compounds, dichlorodifluoromethane, difluoroethane, dimethyl ether, isobutane, n-butane, propane or trichlorofluoromethane. They are preferably present in amounts ranging from 15 to 50% by weight, with respect to the total weight of the composition.

The compositions according to the invention can, in addition, also comprise additional cosmetic and determatological active principles.

Mention may be made, among active principles, of:
vitamins (A, C, E, K, PP, and the like) and their derivatives or precursors, alone or as mixtures;
antiaging agents;
antioxidants;
agents for combating free radicals;
antiglycation agents;
soothing agents;
NO-synthase inhibitors;
agents which stimulate the synthesis of dermal or epidermal macromolecules and/or which prevent their decomposition;
agents which stimulate the proliferation of fibroblasts;
agents which stimulate the proliferation of keratinocytes;
dermo-decontracting agents;
tightening agents;
matifying agents;
keratolytic agents;
desquamating agents;
moisturizing agents, such as, for example, polyols, such as glycerol, butylene glycol or propylene glycol;
agents which act on the energy metabolism of the cells;
insect repellents;
substance P or substance CRGP antagonists;
agents for combating hair loss and/or for the regrowth of the hair;
antiwrinkle agents;
agents which modulate the pigmentation of the skin or hair;
astringent agents;
sebum-regulating agents or antiseborrhoeics.

Of course, a person skilled in the art will take care to choose the optional additional compound or compounds mentioned above and/or their amounts so that the advantageous properties intrinsically attached to the compositions in accordance with the invention are not, or not substantially, detrimentally affected by the envisaged addition or additions.

A person skilled in the art will choose the said active principle or principles according to the effect desired on the skin, hair, eyelashes, eyebrows or nails.

In addition, the composition can comprise at least one ingredient, such as fillers having a soft focus effect or agents which promote the natural colouring of the skin, intended to supplement the biological effect of these active principles or to contribute an immediate visual antiaging effect.

Other Additional Ingredients

In addition, the composition can comprise at least one additional ingredient intended to contribute an immediate visual effect. Mention may in particular be made of agents which promote the naturally pink colouring of the skin.

Mention may be made, as agents which promote the naturally pink colouring of the skin, for example, of self-tanning agents, that is to say an agent which, applied to the skin, in particular to the face, makes it possible to obtain a tanning effect with an appearance more or less similar to that which can result from prolonged exposure to the sun (natural tanning) or under a UV lamp.

Mention may in particular be made, as examples of self-tanning agents, of:
dihydroxyacetone (DHA),
erythrulose, and
the combination of a catalytic system formed of:
manganese and/or zinc salts and oxides, and
alkali metal and/or alkaline earth metal hydrogencarbonates.

The self-tanning agents are generally chosen from mono- or polycarbonyl compounds, such as, for example, isatin, alloxan, ninhydrin, glyceraldehyde, mesotartaric aldehyde, glutaraldehyde, erythrulose, pyrazoline-4,5-dione derivatives, such as described in Patent Applications FR 2 466 492 and WO 97/35842, dihydroxyacetone (DHA) or 4,4-dihydroxypyrazolin-5-one derivatives, such as described in Patent Application EP 903 342. Use will preferably be made of DHA.

The DHA can be used in the free and/or encapsulated form, for example encapsulated in lipid vesicules, such as liposomes, described in particular in Application WO 97/25970.

Generally, the self-tanning agent is present in an amount ranging from 0.01 to 20% by weight and preferably in an amount of between 0.1 and 10% of the total weight of the composition.

Use may also be made of other dyes which make it possible to modify the colour produced by the self-tanning agent.

These dyes can be chosen from synthetic or natural direct dyes.

These dyes can be chosen, for example, from red or orange dyes of the fluoran type, such as those described in Patent Application FR 2 840 806. Mention may be made, for example, of the following dyes:
tetrabromofluorescein or eosin, known under the CTFA name: CI-45380 or Red 21;
phloxine B, known under the CTFA name: CI-45410 or Red 27;
diiodofluorescein, known under the CTFA name: CI-45425 or Orange 10;
dibromofluorescein, known under the CTFA name: CI-45370 or Orange 5;
the sodium salt of tetrabromofluorescein, known under the CTFA name: CI-45380 (Na salt) or Red 22;
the sodium salt of phloxine B, known under the CTFA name: CI-45410 (Na salt) or Red 28;
the sodium salt of diiodofluorescein, known under the CTFA name: CI-45425 (Na salt) or Orange 11;
erythrosine, known under the CTFA name: CI-45430 or Acid Red 51;
phloxine, known under the CTFA name: CI-45405 or Acid Red 98.

These dyes can also be chosen from anthraquinones, caramel, carmine, carbon black, azulene blues, methoxsalen, trioxsalen, guaiazulene, chamazulene, rose to bengal, eosin 10B, cyanosine or daphinine.

These dyes can also be chosen from indole derivatives, such as monohydroxy-indoles, such as described in Patent FR 2 651 126 (i.e.: 4-, 5-, 6- or 7-hydroxyindole), or dihydroxy-indoles, such as described in Patent EP-B-0 425 324 (i.e.: 5,6-dihydroxyindole, 2-methyl-5,6-dihydroxyindole, 3-methyl-5,6-dihydroxyindole or 2,3-dimethyl-5,6-dihydroxyindole).

The examples which follow serve to illustrate the invention, but without having any limiting character. In these examples, the amounts of the ingredients of the compositions are given as % by weight, with respect to the total weight of the composition.

SYNTHETIC EXAMPLES

Example 1

Preparation of butyl (2E,4E)-5-[bis(2-hydroxyethyl)amino]-2-cyanopenta-2,4-dienoate

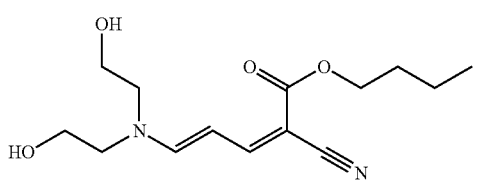

(o)

First Stage: Preparation of butyl (2E,4E)-5-[acetyl(phenyl)amino]-2-cyanopenta-2,4-dienoate 3-Anilinoacrolein-aniline (3 g, 13.5×10$^{-3}$ mol) and n-butyl cyanoacetate (1.9 ml, 13.5×10$^{-3}$ mol) are heated in 6 ml of acetic anhydride for 1 hour 30 minutes at 85-90° C. while bubbling with nitrogen. After cooling, 10 ml of methanol are added and precipitation is allowed to take place. The solid obtained is filtered off and rinsed with methanol. Drying is carried out. 3.14 g (yield: 74%) of a yellow powder of butyl (2E,4E)-5-[acetyl(phenyl)amino]-2-cyanopenta-2,4-dienoate are recovered, which powder is used as is in the following stage.

Second Stage: Preparation of the Compound of Example 1

A solution of the preceding product (3.1 g, 0.01 mol) and of diethanolamine (1.04 g, 0.01 mol) in 6 ml of acetonitrile is brought to reflux for 4 hours. After cooling, the mixture is evaporated to dryness under vacuum. The orange-coloured residue is chromatographed on a silica column (gradient of eluents: CH$_2$Cl$_2$/MeOH 100:0 to 90:10). 1.32 g (yield: 47%) of the pure fractions of the derivative of Example 1 are thus obtained in the form of a pale yellow powder:

M.P.: 50-52° C.

UV (Ethanol): $\lambda_{max}$=382 nm, E1%=2270.

Example 2

Preparation of hexyl (2E,4E)-5-[bis(2-hydroxyethyl)amino]-2-cyanopenta-2,4-dienoate

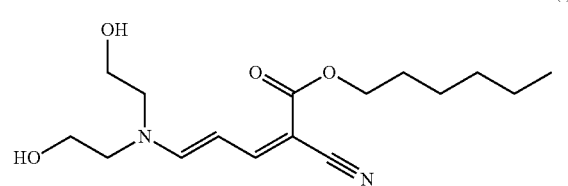

(t)

First Stage: Preparation of hexyl (2E,4E)-5-[acetyl(phenyl)amino]-2-cyanopenta-2,4-dienoate 3-Anilinoacrolein-aniline (2 g, 9×10$^{-3}$ mol) and n-hexyl cyanoacetate (1.52 g, 9×10$^{-3}$ mol) are heated in 5 ml of acetic anhydride at 105° C. for 3 hours while bubbling with nitrogen. After cooling, 10 ml of methanol are added and precipitation is allowed to take place. The solid obtained is filtered off and rinsed with methanol. Drying is carried out. 1.2 g of a yellow powder (yield: 32%) of hexyl (2E,4E)-5-[acetyl(phenyl)amino]-2-cyanopenta-2,4-dienoate are recovered, which powder is used as is in the following stage.

Second Stage: Preparation of the Compound of Example 2

A solution of the preceding product (1 g, 2.94×10$^{-3}$ mol) and of diethanolamine (0.31 g, 2.94×10$^{-3}$ mol) in 5 ml of acetonitrile is brought to reflux for 1 hour 15 minutes. After cooling, the mixture is evaporated to dryness under vacuum. The brown residue obtained is chromatographed on a silica column (gradient of eluents: CH$_2$Cl$_2$/MeOH 100:0 to 98:2). 0.51 g (yield: 55%) of the pure fractions of the derivative of Example 2 is thus obtained in the form of a pale yellow powder:

M.P.: 76-78° C.

UV (Ethanol): $\lambda_{max}$=381 nm, E1%=1846.

Example 3

Preparation of n-octyl (2E,4E)-5-[bis(2-hydroxyethyl)amino]-2-cyanopenta-2,4-dienoate

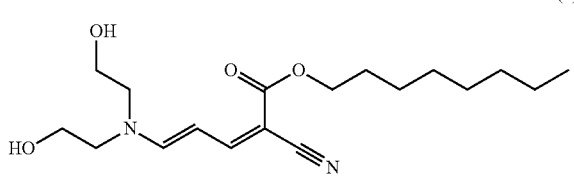

(u)

First Stage: Preparation of n-octyl (2E,4E)-5-[acetyl(phenyl)amino]-2-cyanopenta-2,4-dienoate 3-Anilinoacrolein-aniline (27.7 g, 0.125 mol) and n-octyl cyanoacetate (26.3 ml, 0.125 mol) are heated in 70 ml of acetic anhydride at 115° C. for 2 hours while bubbling with nitrogen. After cooling, 80 ml of methanol are added and precipitation is allowed to take place. The solid obtained is filtered off and rinsed with methanol. Drying is carried out. 36.4 g of a yellow powder (yield: 79%) of butyl (2E,4E)-5-[acetyl(phenyl)amino]-2-cyanopenta-2,4-dienoate are recovered, which powder is used as is in the following stage.

Second Stage: Preparation of the Compound of Example 3

A solution of the preceding product (36.2 g, 0.00982 mol) and of diethanolamine (10.33 g, 0.00982 mol) in 75 ml of acetonitrile is brought to reflux for 1 hour 30 minutes. After cooling in an ice bath, the product precipitates. The solid is filtered off and rinsed with a piston of cold acetonitrile. The solid is recrystallized twice from ethyl ether. 18.9 g (yield: 57%) of the derivative of Example 3 are thus obtained in the form of a pale yellow powder:

M. P.: 81-84° C.

UV (Ethanol): $\lambda_{max}$=382 nm, E1%=1725.

Example 4

Preparation of n-octyl (2E,4E)-2-cyano-5-(diethylamino)penta-2,4-dienoate

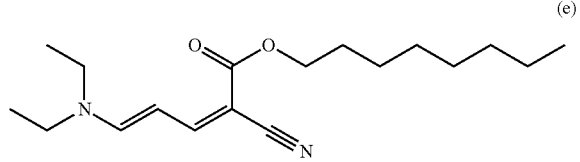 [SMILES: CCCCCCCCOC(=O)/C(C#N)=C\C=C\N(CC)CC]

(e)

Diethylamine (14.5 ml, 0.14 mol) and propargyl alcohol (6.81 ml, 0.117 mol) are dissolved in 100 ml of toluene. 34.5 g of manganese dioxide (activated, <5 µm; 3.4 equiv.) are added portionwise while controlling the strong exotherm (temperature <50° C.) and the mixture is left stirring at 52° C. for 20 hours. The reaction mixture is filtered. The yellow filtrate is poured into a reactor surmounted by a Dean and Stark apparatus. n-Octyl cyanoacetate (23 g, 0.117 mol) and catalyst (0.1 equiv., 0.667 ml of acetic acid and 1.2 ml of N,N-diethylamine) are added with stirring and the reaction mixture is brought to reflux. It is left at reflux for 5 hours 30 minutes. After cooling, dichloromethane is added and washing is carried out once with a saturated sodium bicarbonate solution and then once with water. The organic phase is dried and then concentrated under vacuum. The brown red oil obtained is chromatographed on a silica column (gradient of eluents: heptane/AcOEt 90:10 to 80:20). 26 g (yield: 72%) of the pure fractions of the derivative of Example 4 are thus obtained in the form of an orange-coloured gum which crystallizes; recrystallization from heptane gave the derivative of Example 4 in the form of a yellow powder:

M.P.: 48-49° C.

UV (Ethanol): $\lambda_{max}$=381 nm, E1%=2274.

Example 5

Preparation of 2-ethylhexyl (2E,4E)-2-cyano-5-(diethylamino)-penta-2,4-dienoate

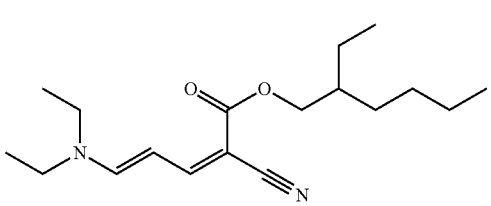

(g)

Diethylamine (30 g, 0.41 mol) and propargyl alcohol (18.4 g, 0.328 mol) are dissolved in 250 ml of toluene. 72.6 g of manganese dioxide (activated, <5 µm; 2.5 equiv.) are added portionwise while controlling the strong exotherm (temperature <50° C.) and the mixture is left stirring at 90° C. for 5 hours. The reaction mixture is filtered. The yellow filtrate is poured into a reactor surmounted by a Dean and Stark apparatus. 2-Ethylhexyl cyanoacetate (61.5 g, 0.312 mol) and catalyst (0.1 equiv., 1.77 ml of acetic acid and 3.2 ml of N,N-diethylamine) are added with stirring and the reaction mixture is brought to reflux. It is left at reflux for 5 hours 30 minutes. After cooling, 500 ml of dichloromethane are added and washing is carried out once with a saturated sodium bicarbonate solution and then twice with water. The organic phase is dried and then purified on a silica bed. The first fractions are recovered and concentrated under vacuum. 21.9 g (yield: 23%) of the pure fractions of the derivative of Example 5 are thus obtained in the form of an orange-coloured gum which crystallizes; recrystallization from heptane gave the derivative of Example 5 in the form of a yellow powder

M.P.: 32-37° C.

UV (Ethanol): $\lambda_{max}$=381 nm, E1%=2240.

Example 6

Preparation of methyl (2E,4E)-2-cyano-5-(dimethylamino)-penta-2,4-dienoate

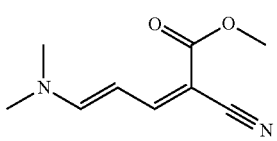

(z)

N,N-Dimethylacrolein (80.52 ml, 0.772 mol) is dissolved in 460 ml of toluene while bubbling with nitrogen and the catalyst, a mixture of acetic acid (8.85 ml, 0.2 equiv.) and of n-octylamine (3.83 ml, 0.03 equiv.), is added. The mixture is heated to reflux and methyl cyanoacetate (69.48 ml, 0.787 mol) is added dropwise over 45 minutes. The water is removed by azeotropic distillation. The reaction is halted after 2 hours 30 minutes. The solvent is evaporated under vacuum. 152 g of a light brown powder are obtained, which powder is crystallized from isopropanol to give 118.5 g (yield: 85%) of the derivative of Example 6 in the form of a pale yellow powder M.P.: 158-159° C.
UV (Ethanol): $\lambda_{max}$=378 nm, E1%=3564.

Example 7

Preparation of octyl (2E,4E)-2-cyano-5-(dimethylamino)penta-2,4-dienoate

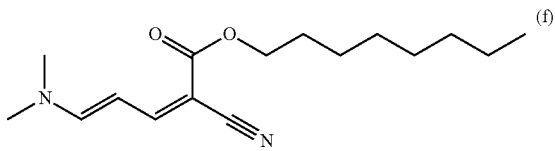 [SMILES: CCCCCCCCOC(=O)/C(C#N)=C\C=C\N(C)C]
(f)

N,N-Dimethylacrolein (37.4 ml, 0.374 mol) is dissolved in 500 ml of toluene while bubbling with nitrogen and the catalyst, a mixture of acetic acid (4.1 ml, 0.2 equiv.) and of n-octylamine (1.8 ml, 0.03 equiv.), is added. The mixture is heated to reflux and n-octyl cyanoacetate (76 ml, 0.359 mol) is added dropwise over 25 minutes. The water is removed by azeotropic distillation. The reaction is halted after 2 hours. The solvent is evaporated under vacuum. 123 g of an orangey brown solid are obtained, which solid is recrystallized from isopropanol to give 118.5 g (yield: 85%) of the derivative of Example 7 in the form of pale yellow needles:
M.P.: 80-81° C.
UV (Ethanol): $\lambda_{max}$=380 nm, E1%=2186.

Example 8

Preparation of 2,3-dihydroxypropyl (2E,4E)-2-cyano-5-(dimethylamino)penta-2,4-dienoate)

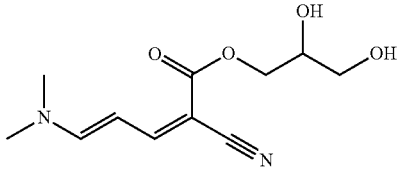
(w)

First Stage: Preparation of (2,2-dimethyl-1,3-dioxolan-4-yl)methyl cyanoacetate

A mixture of methyl cyanoacetate (1.3 ml, 15×10⁻³ mol), of solketal (1.25 ml, 10×10⁻³ mol) and of DMAP (2.7 mg, 0.03 equiv.) is heated at reflux with stirring for 30 hours in a reactor rendered inert with nitrogen. After cooling, the solvent is evaporated under vacuum and the brown oil obtained is chromatographed on a silica column (gradient of eluents: heptane/EtOAc from 90:10 to 80:20). 423 mg (yield: 23%) of the pure fractions of (2,2-dimethyl-1,3-dioxolan-4-yl)methyl cyanoacetate are thus obtained in the form of a yellow oil used as is in the following stage.

Second Stage: Preparation of (2,2-dimethyl-1,3-dioxolan-4-yl)methyl (2E,4E)-2-cyano-5-(dimethylamino)penta-2,4-dienoate The preceding product (50 mg, 0.254×10⁻³ mol) and the catalysts, n-octylamine (1.3 µl, 0.03 equiv.) and acetic acid (3 µl, 0.2 equiv.), in 0.8 ml of toluene are brought to reflux in a reactor rendered inert with nitrogen. N,N-Dimethylacrolein (26 µl, 0.25×10⁻³ mol), dissolved in 0.8 ml of toluene, is added dropwise to the reaction mixture. Reflux is maintained for 36 hours while adding the same amounts of catalyst every 8 hours. After cooling, the solvent is evaporated under vacuum and the brown paste obtained is crystallized from 2 ml of isopropanol. 68 mg (yield: 97%) of (2,2-dimethyl-1,3-dioxolan-4-yl)methyl (2E,4E)-2-cyano-5-(dimethylamino) penta-2,4-dienoate are thus obtained in the form of a beige powder used as is in the following stage:
UV (Ethanol): $\lambda_{max}$=379 nm, E1%=1974.

Third Stage: Preparation of the Compound of Example 8

The preceding product (60 mg, 0.21×10⁻³ mol) is dissolved in an MeOH/THF 1:1 mixture in a reactor rendered inert with nitrogen. Dowex H+ (1 g) is added thereto and the mixture is left stirring for 24 hours. After filtering off the Dowex and evaporating the solvents, the residue is chromatographed on a silica column (eluent: $CH_2Cl_2$/MeOH 95:5). 22 mg (yield: 43%) of the pure fractions of the derivative of Example 8 are thus obtained in the form of a viscous orange-coloured oil:
UV (Ethanol): $\lambda_{max}$=375 nm, E1%=1485.

Example 9

Preparation of n-octyl (2E,4E)-2-cyano-5-(piperidin-1-yl)penta-2,4-dienoate

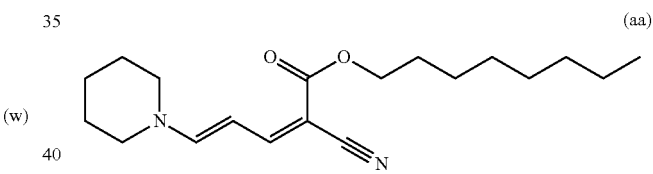
(aa)

The derivative of Example 4 (15.5 g, 0.051 mol) is heated at 60° C. for 2 hours with 100 ml of piperidine while bubbling with nitrogen. Heating is continued at 80° C. for 6 hours. After cooling the reaction mixture, it is poured into 2 liters of water. The precipitate obtained is filtered off and is washed with 3 pistons of water. After drying, 12.57 g (yield: 75%) of the derivative of Example 9 are obtained in the form of a pale yellow powder:
M.P.: 87-89° C.
UV (Ethanol): $\lambda_{max}$=382 nm, E1%=2270.

FORMULATION EXAMPLES

The following oil/water emulsions are prepared; the amounts are expressed as percentages by weight, with respect to the total weight of each composition.

| Composition | Formulation 1 | Formulation 2 |
| --- | --- | --- |
| Polydimethylsiloxane | 0.5 | 0.5 |
| Preservatives | 1 | 1 |
| Stearic acid | 1.5 | 1.5 |
| Glyceryl monostearate/PEG (100 EO) stearate mixture | 1 | 1 |

-continued

| Composition | Formulation 1 | Formulation 2 |
|---|---|---|
| Mixture of cetearyl glucoside and of cetyl and stearyl alcohols | 2 | 2 |
| Cetyl alcohol | 0.5 | 0.5 |
| 4-(tert-Butyl)-4'-methoxydibenzoyl-methane | 2 | 2 |
| $C_{12}/C_{15}$ Alkyl benzoate | 10 | 10 |
| Derivative of Example 4: compound (e) | 1 | 2 |
| Deionized water | q.s. for 100 | q.s. for 100 |
| Complexing agent | 0.1 | 0.1 |
| Glycerol | 5 | 5 |
| Xanthan gum | 0.2 | 0.2 |
| Monocetyl phosphate | 1 | 1 |
| Isohexadecane | 1 | 1 |
| Acrylic acid/stearyl methacrylate copolymer | 0.2 | 0.2 |
| Triethanolamine | q.s. for pH | q.s. for pH |

Procedure:

The aqueous phase (Phase B) comprising all of its ingredients is heated to 80° C. in a water bath. The fatty phase (Phase A) comprising all of its ingredients is heated to 80° C. in a water bath. A is emulsified in B with stirring of rotor-stator type (device from Moritz). Phase C is incorporated and the mixture is allowed to return to ambient temperature with moderate stirring. The triethanolamine is introduced so as to adjust the pH to the value desired at the end of manufacture.

Tests of Photostability of the Dibenzoylmethane Screening Agent

The following emulsions are prepared:

Formulations Ai (Invention):

| | |
|---|---|
| Cetearyl glucoside/cetearyl alcohol mixture (Montanov 68) | 7.5 g |
| $C_{12}/C_{15}$ Alkyl benzoate (Witconol TN, Witco) | 20 g |
| Compound of the invention (compound (e), (f) or (g)) | 2 g |
| 4-(tert-Butyl)-4'-methoxydibenzoylmethane (avobenzone) | 1 g |
| Glycerol | 5 g |
| Preservatives | q.s. |
| Demineralized water | q.s. for 100 g |

Formulations Bi (Outside the Invention):

| | |
|---|---|
| Cetearyl glucoside/cetearyl alcohol mixture (Montanov 68) | 7.5 g |
| $C_{12}/C_{15}$ Alkyl benzoate (Witconol TN, Witco) | 20 g |
| Comparative compound (compound $b_1$, $b_2$, $b_3$ or $b_4$ outside the invention) | 2 g |
| 4-(tert-Butyl)-4'-methoxydibenzoylmethane (avobenzone) | 1 g |
| Glycerol | 5 g |
| Preservatives | q.s. |
| Demineralized water | q.s. for 100 g |

Approximately 20 mg of the preceding emulsion are spread over 10 cm² of the surface of a ground silica disc; the exact amount of the deposited layer is determined by weighing.

The films of the solutions are irradiated for 1 hour using an Oriel solar simulator (UV-A flux=14.4 mW/cm²; UV-B flux=0.43 mW/cm²) with a dose of 12 J/cm² and are then extracted with 10 ml of ethanol comprising 10% of isopropanol and subjected to ultrasound for 5 min. The products are quantified by HPLC of the extracts.

The degrees of loss are determined by comparison of the amounts of product present in the irradiated samples and in the non-irradiated controls prepared simultaneously and treated in the same way (means over 3 samples).

Photostability Results

Comparative Example $b_1$

Family of the Cyclic Dicyano Compounds

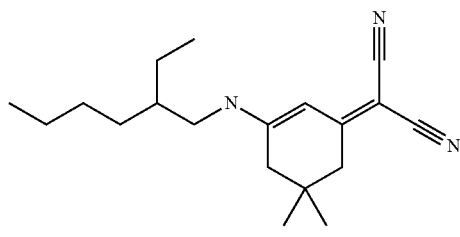

RN = 110186-47-5

Comparative Example $b_2$

Family of the Cyclic Dicyano Compounds

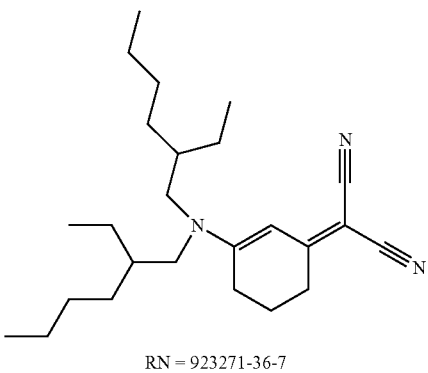 [SMILES: CCCCC(CC)CN(CC(CC)CCCC)C1=CC(=C(C#N)C#N)CCC1]

RN = 923271-36-7

Comparative Example $b_3$

Family of the Cyclic Cyanoacetates

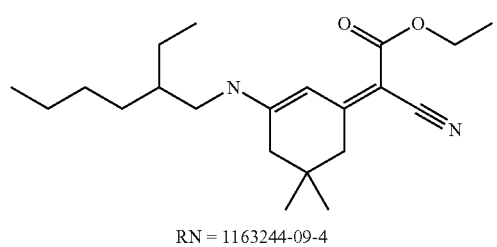 [SMILES: CCCCC(CC)CNC1=C/C(=C(/C#N)C(=O)OCC)CC(C)(C)C1]

RN = 1163244-09-4

Comparative Example b₄

Family of the Phenyl Sulphone Acetates

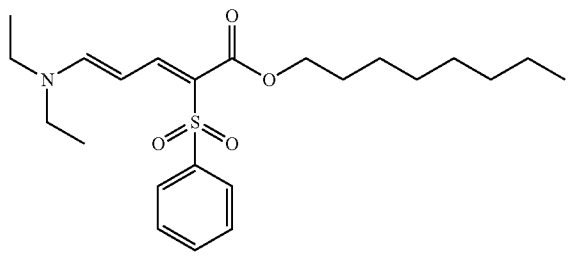

RN = 98835-90-6

| TABLE OF THE PHOTOSTABILITY RESULTS | | |
|---|---|---|
| Composition tested | % of disappearance of the avobenzone (mean loss) | % of disappearance of the merocyanine compound (mean loss) |
| Formulation A₁ (invention): 1% avobenzone + 2% compound (e) | 1.6% | 1.1% |
| Formulation A₂ (invention): 1% avobenzone + 2% compound (f) | 7.0% | 7.0% |
| Formulation A₃ (invention): 1% avobenzone + 2% compound (g) | 6.8% | 3.5% |
| Formulation B₁ (outside the invention) 1% avobenzone + 2% compound (b₁) | 27.5% | 21.6% |
| Formulation B₂ (outside the invention) 1% avobenzone + 2% compound (b₂) | 17.3% | 20.0% |
| Formulation B₃ (outside the invention) 1% avobenzone + 2% compound (b₃) | 18.1% | 21.7% |
| Formulation B₄ (outside the invention) 1% avobenzone + 2% compound (b₄) | 14.4% | 15.4% |

The compounds of the invention (e), (f) and (g) respectively present in the formulations A₁ to A₃ photostabilize the avobenzone better than the comparative compounds b₁, b₂, b₃ and b₄ present in the formulations B₁ to B₄ and do this in a significant way.
The compounds of the invention (e), (f) and (g) respectively present in the formulations A₁ to A₃ do not or virtually do not photodecompose in the presence of avobenzone, in contrast to the comparative compounds b₁, b₂, b₃ and b₄.

The invention claimed is:
1. Composition comprising, in a cosmetically acceptable vehicle, at least one UV screening system, characterized in that it comprises:
(1) at least one dibenzoylmethane derivative and
(2) an amount effective for photostabilizing the composition of at least one merocyanine dicyano or cyanoacetate derivative chosen from the group consisting of:
(i) those corresponding to the following general formula (I):

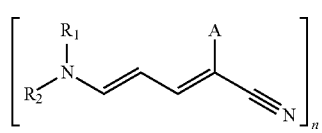

(I)

in which:
A is the —C≡N or —(C═O)OR₃ group,
R₁ and R₂, which are identical or different, denote a linear or branched $C_1$-$C_3$ alkyl radical, the hydroxyethyl group or a $C_5$-$C_6$ cycloalkyl,
R₃ denotes a linear or branched $C_1$-$C_8$ alkyl radical,
n is 1 or 2;

with the proviso that, when n=2, R₁, R₂ or R₃ is a $C_2$-$C_{16}$ alkyl diradical or else R₁ and R₂ form, with 2 nitrogen atoms, a cyclic divalent —(CH₂)$_m$— radical with m being an integer ranging from 3 to 7;

(ii) the compound (a):

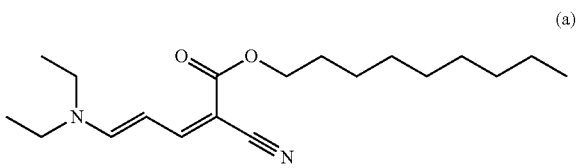 [SMILES: CCCCCCCCCOC(=O)/C(C#N)=C\C=C\N(CC)CC]

(a)

(iii) the compound (b):

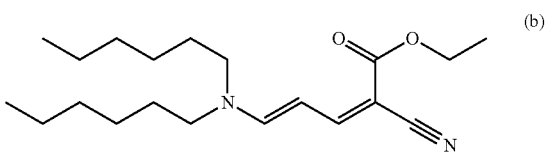 [SMILES: CCCCCCN(/C=C/C=C(/C#N)C(=O)OCC)CCCCCC]

(b)

(iv) the compound (c):

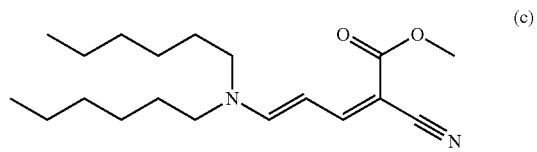 [SMILES: CCCCCCN(/C=C/C=C(/C#N)C(=O)OC)CCCCCC]

(c)

(v) the compound (l):

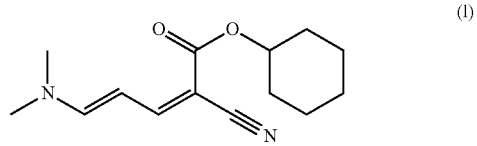 [SMILES: CN(C)/C=C/C=C(/C#N)C(=O)OC1CCCCC1]

(l)

(vi) the compound (p):

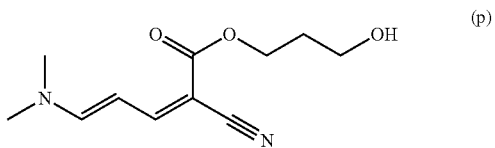 [SMILES: CN(C)/C=C/C=C(/C#N)C(=O)OCCCO]

(p)

(vii) the compound (v):

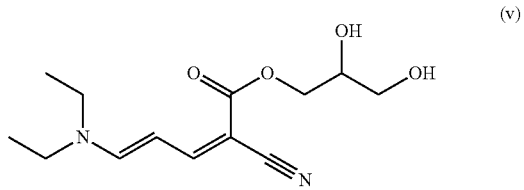 [SMILES: CCN(/C=C/C=C(/C#N)C(=O)OCC(O)CO)CC]

(v)

(viii) the compound (w):
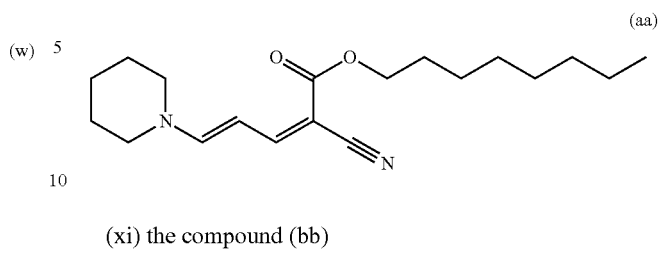
(w)
(x) the compound (aa)
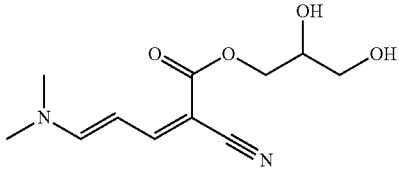
(aa)
(ix) the compound (x):
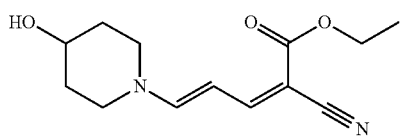
(x)
(xi) the compound (bb)
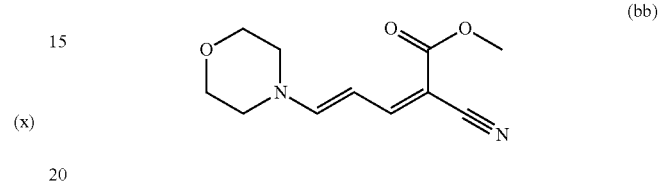
(bb)
and their E,E-, E,Z- or Z,Z-geometrical isomeric forms.
2. Composition according to claim 1, where the compound or compounds of formula (I) are chosen from those of the following formulae and their E,E-, E,Z- or Z,Z-isomers:
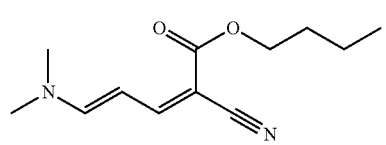
(d)
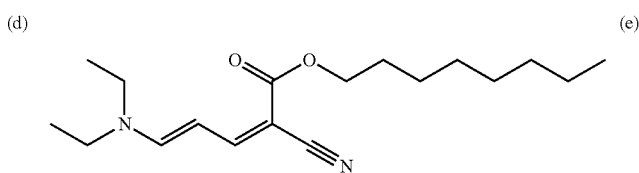
(e)
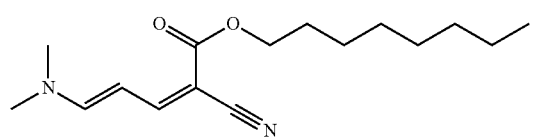
(f)
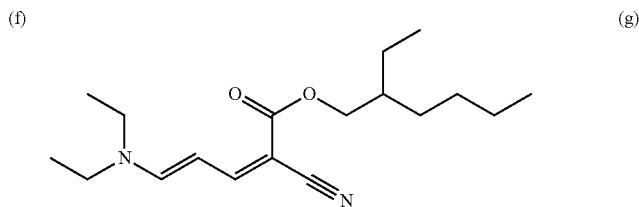
(g)
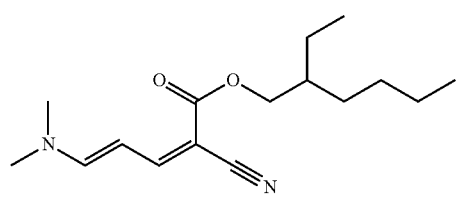
(h)
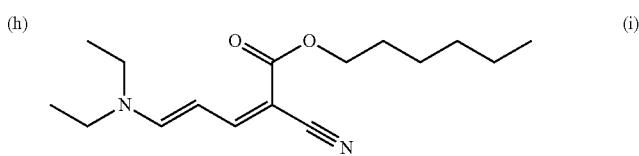
(i)
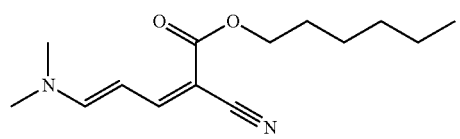
(j)
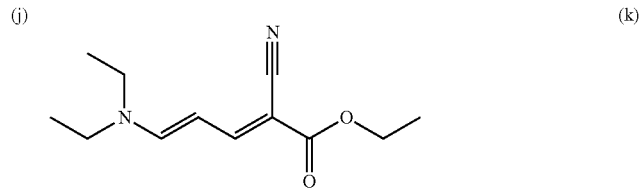
(k)
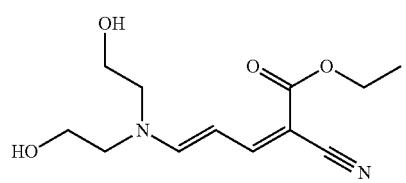
(m)
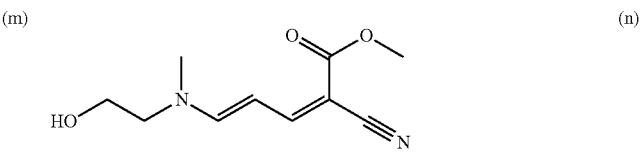
(n)

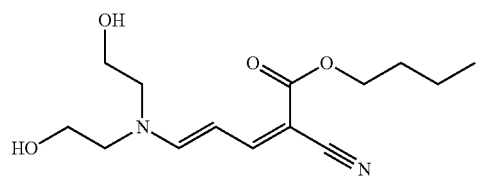
(o)
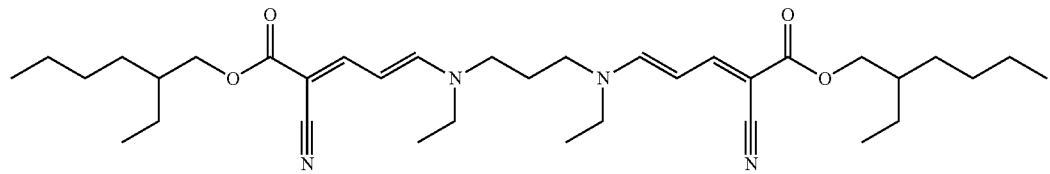
(q)
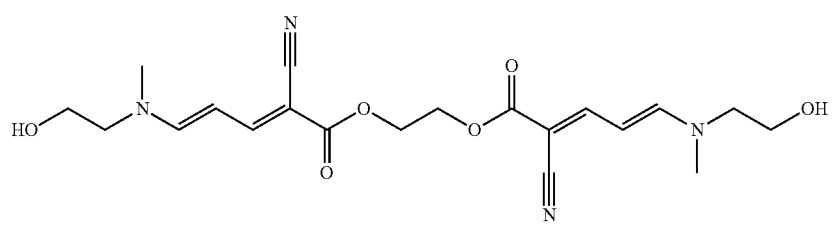
(r)
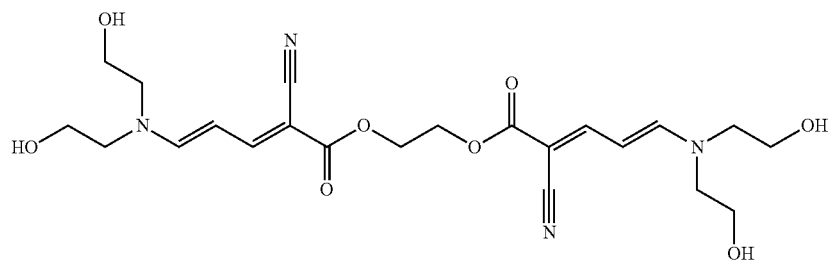
(s)
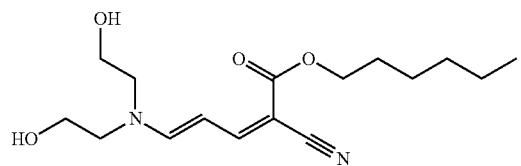
(t)
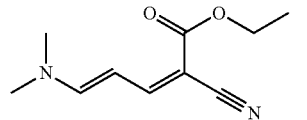
(u)
(y)
(z)
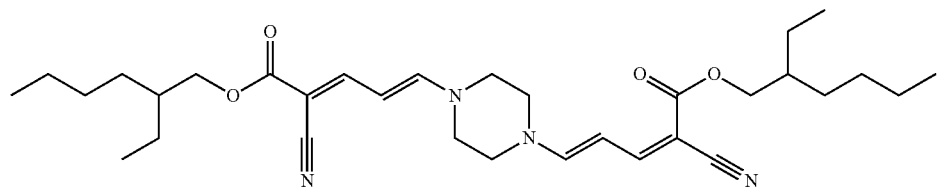
(cc)
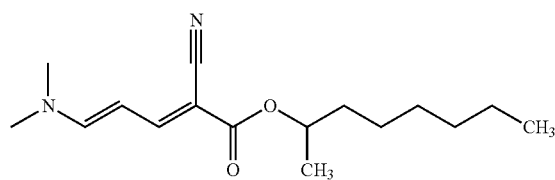
(ee)

(ff) 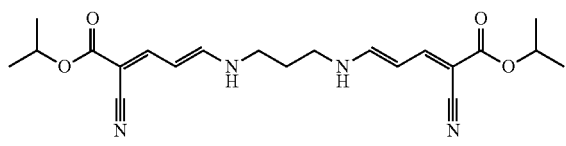

(gg) 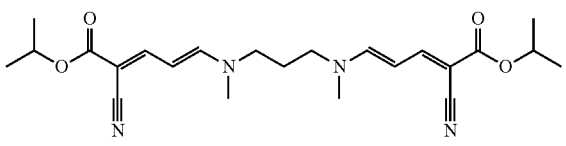

(hh) 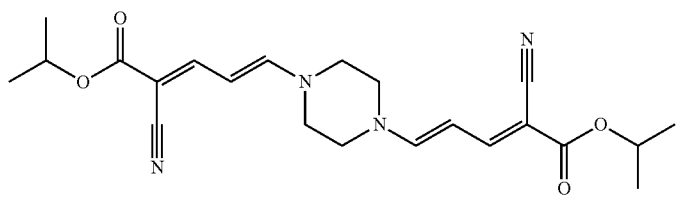

3. Composition according to claim 1, where the merocyanine dicyano or cyanoacetate derivative or derivatives are chosen from the following compounds or their isomeric forms:

(e) 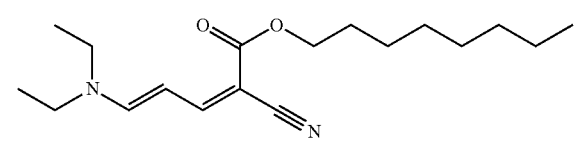

(f) 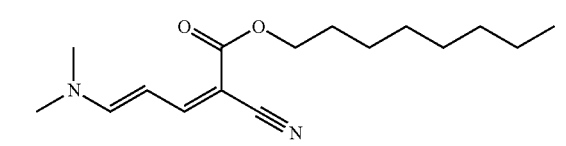

(g) 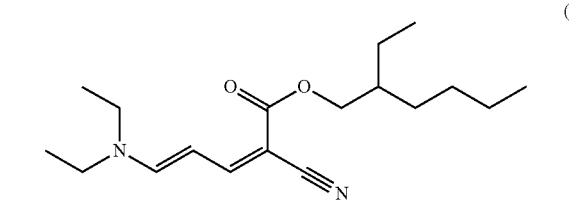

(h) 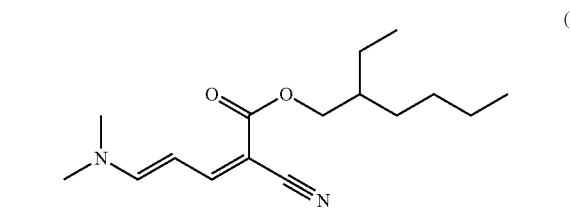

(t) 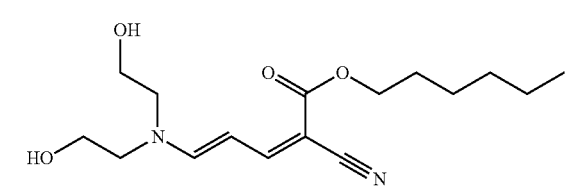

(u) 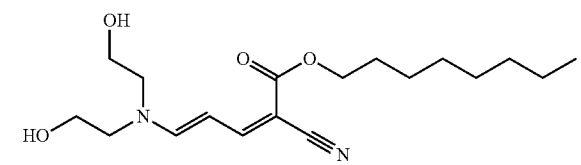

(aa) 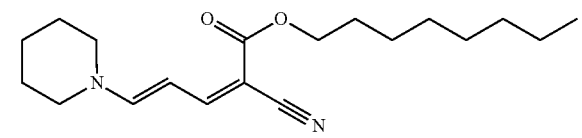

(ee) 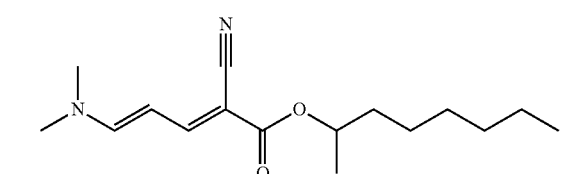

(gg) 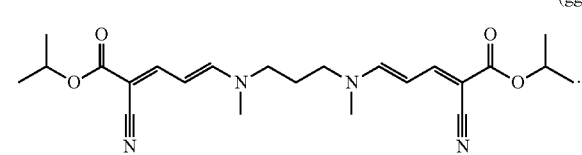

4. Composition according to claim 1, where the dibenzoylmethane derivative is 4-(tert-butyl)-4'-methoxydibenzoylmethane or Butyl Methoxy Dibenzoylmethane or avobenzone in the following formula:

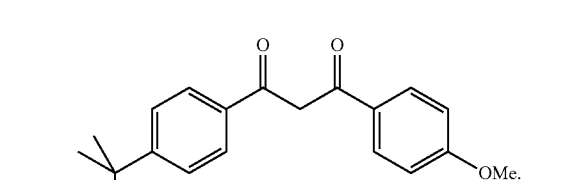

5. Composition according to claim 1, wherein it additionally comprises other additional organic or inorganic screening agents which are active in the UV-A and/or UV-B regions and which are water-soluble or fat-soluble or else insoluble in the cosmetic solvents commonly used.

6. Composition according to claim 5, where the additional organic screening agents are chosen from anthranilics; cinnamic derivatives; salicylic derivatives, benzylidenecamphor derivatives; benzophenone derivatives; β,β-diphenylacrylate derivatives; triazine derivatives; phenylbenzotriazole derivatives; benzalmalonate derivatives; phenylbenzimidazole derivatives; imidazolines; bis-benzazolyl derivatives; p-aminobenzoic acid (PABA) derivatives; methylenebis(hydroxyphenylbenzotriazole) derivatives; benzoxazole derivatives; screening polymers and screening silicones; dimers derived from α-alkylstyrene; 4,4-diarylbutadienes; merocyanine derivatives other than those of formula (I), (a), (b), (c), (l), (p), (v), (w), (x), (aa) and (bb); and their mixtures.

7. Composition according to claim 5, wherein the organic UV screening agent or agents are chosen from the following compounds:
Ethylhexyl Methoxycinnamate,
Homosalate,
Ethylhexyl Salicylate,
Octocrylene,
Phenylbenzimidazole Sulfonic Acid,
Benzophenone-3,
Benzophenone-4,
Benzophenone-5,
n-Hexyl 2-(4-diethylamino-2-hydroxybenzoyl)benzoate,
1,1'-(1,4-Piperazinediyl)bis[1-[2-[4-(diethylamino)-2-hydroxybenzoyl]phenyl]-methanone]
4-Methylbenzylidene Camphor,
Terephthalylidene Dicamphor Sulfonic Acid,
Disodium Phenyl Dibenzimidazole Tetrasulfonate,
Ethylhexyl Triazone,
Bis-Ethylhexyloxyphenol Methoxyphenyl Triazine,
Diethylhexyl Butamido Triazone,
2,4,6-Tris(biphenyl-4-yl)-1,3,5-triazine,
2,4,6-Tris(dineopentyl 4'-aminobenzalmalonate)-s-triazine,
2,4,6-Tris-(diisobutyl 4'-aminobenzalmalonate)-s-triazine,
2,4-Bis(dineopentyl 4'-aminobenzalmalonate)-6-(n-butyl 4'-aminobenzoate)-s-triazine,
2,4-Bis(n-butyl 4'-aminobenzoate)-6-[(3-{1,3,3,3-tetramethyl-1-[(trimethylsilyl)-oxy]disiloxanyl}propyl) amino]-s-triazine,
Methylene Bis-Benzotriazolyl Tetramethylbutylphenol,
Drometrizole Trisiloxane,
Polysilicone-15,
Dineopentyl 4'-methoxybenzalmalonate,
1,1-Dicarboxy(2,2'-dimethylpropyl)-4,4-diphenylbutadiene,
2,4-Bis[5-1(dimethylpropyl)benzoxazol-2-yl-(4-phenyl)imino]-6-(2-ethylhexyl)imino-1,3,5-triazine,
and their mixtures.

8. Composition according to claim 5, wherein the additional inorganic screening agents are coated or uncoated metal oxide pigments.

9. Composition according to claim 1, wherein it is provided in the form of an oil-in-water or water-in-oil emulsion.

10. Method for improving the chemical stability with regard to UV radiation of at least one dibenzoylmethane derivative as defined in any one of the preceding claims, characterized in that the said dibenzoylmethane derivative is combined with an effective amount of at least one merocyanine dicyano or cyanoacetate derivative or one of its E,E-, E,Z- or Z,Z-isomeric forms as defined in claim 1.

11. Composition according to claim 2, where the merocyanine dicyano or cyanoacetate derivative or derivatives are chosen from the following compounds or their isomeric forms:

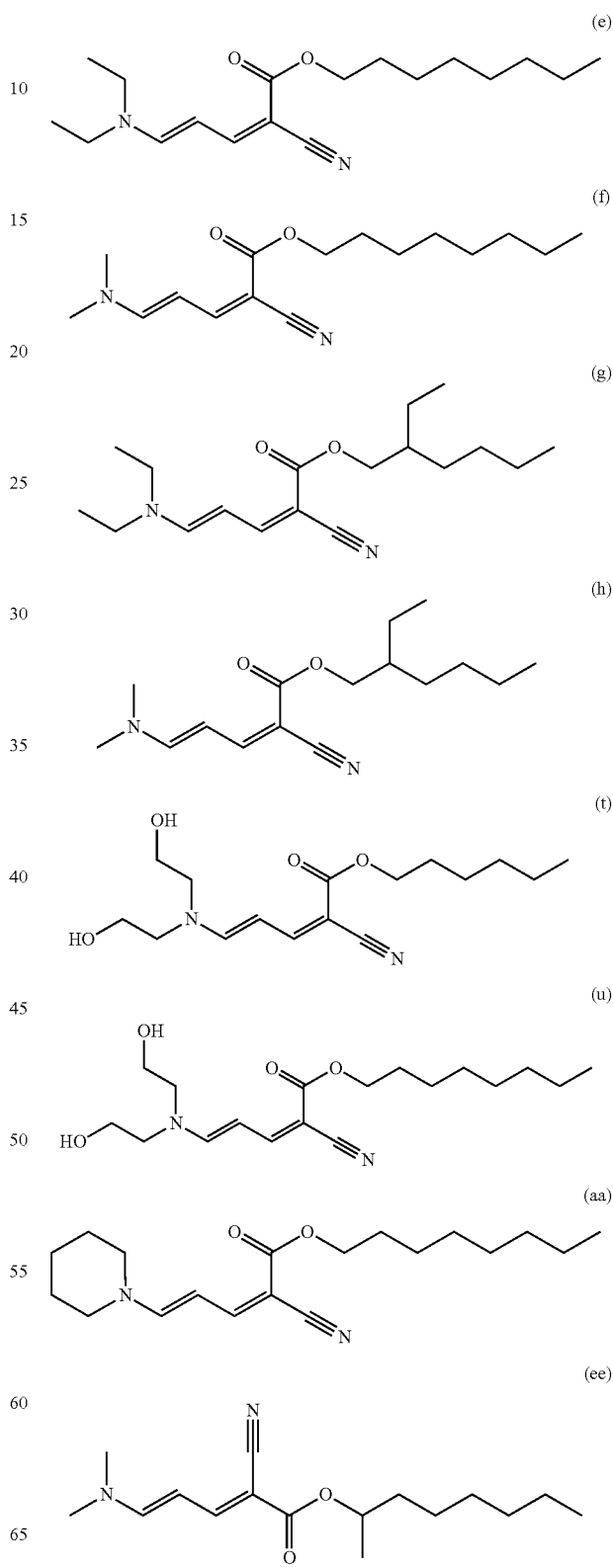

-continued

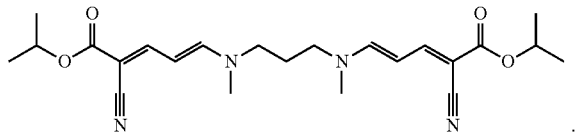
(gg)

12. Composition according to claim 2, where the dibenzoylmethane derivative is 4-(tert-butyl)-4'-methoxydibenzoylmethane or Butyl Methoxy Dibenzoylmethane or avobenzone in the following formula:

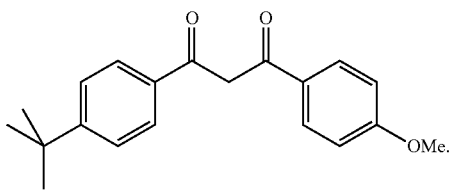 [SMILES: COc1ccc(C(=O)CC(=O)c2ccc(C(C)(C)C)cc2)cc1]

13. Composition according to claim 3, where the dibenzoylmethane derivative is 4-(tert-butyl)-4'-methoxydibenzoylmethane or Butyl Methoxy Dibenzoylmethane or avobenzone in the following formula:

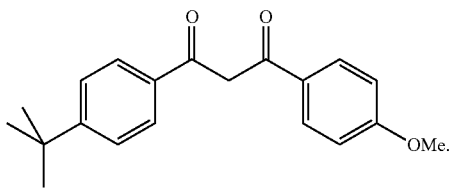 [SMILES: COc1ccc(C(=O)CC(=O)c2ccc(C(C)(C)C)cc2)cc1]

14. Composition according to claim 2, wherein it additionally comprises other additional organic or inorganic screening agents which are active in the UV-A and/or UV-B regions and which are water-soluble or fat-soluble or else insoluble in the cosmetic solvents commonly used.

15. Composition according to claim 3, wherein it additionally comprises other additional organic or inorganic screening agents which are active in the UV-A and/or UV-B regions and which are water-soluble or fat-soluble or else insoluble in the cosmetic solvents commonly used.

16. Composition according to claim 4, wherein it additionally comprises other additional organic or inorganic screening agents which are active in the UV-A and/or UV-B regions and which are water-soluble or fat-soluble or else insoluble in the cosmetic solvents commonly used.

17. Composition according to claim 6, wherein the organic UV screening agent or agents are chosen from the following compounds:

Ethylhexyl Methoxycinnamate,
Homosalate,
Ethylhexyl Salicylate,
Octocrylene,
Phenylbenzimidazole Sulfonic Acid,
Benzophenone-3,
Benzophenone-4,
Benzophenone-5,
n-Hexyl 2-(4-diethylamino-2-hydroxybenzoyl)benzoate,
1,1'-(1,4-Piperazinediyl)bis[1-[2-[4-(diethylamino)-2-hydroxybenzoyl]phenyl]-methanone]
4-Methylbenzylidene Camphor,
Terephthalylidene Dicamphor Sulfonic Acid,
Disodium Phenyl Dibenzimidazole Tetrasulfonate,
Ethylhexyl Triazone,
Bis-Ethylhexyloxyphenol Methoxyphenyl Triazine,
Diethylhexyl Butamido Triazone,
2,4,6-Tris(biphenyl-4-yl)-1,3,5-triazine,
2,4,6-Tris(dineopentyl 4'-aminobenzalmalonate)-s-triazine,
2,4,6-Tris-(diisobutyl 4'-aminobenzalmalonate)-s-triazine,
2,4-Bis(dineopentyl 4'-aminobenzalmalonate)-6-(n-butyl 4'-aminobenzoate)-s-triazine,
2,4-Bis(n-butyl 4'-aminobenzoate)-6-[(3-{1,3,3,3-tetramethyl-1-[(trimethylsilyl)-oxy]disiloxanyl}propyl)amino]-s-triazine,
Methylene Bis-Benzotriazolyl Tetramethylbutylphenol,
Drometrizole Trisiloxane,
Polysilicone-15,
Dineopentyl 4'-methoxybenzalmalonate,
1,1-Dicarboxy(2,2'-dimethylpropyl)-4,4-diphenylbutadiene,
2,4-Bis[5-1(dimethylpropyl)benzoxazol-2-yl-(4-phenyl)imino]-6-(2-ethylhexyl)imino-1,3,5-triazine,
and their mixtures.

18. The composition according to claim 1, where the at least one dibenzoylmethane derivative is present in an amount of 0.01 to 20% by weight based upon the total weight of the composition and the at least one merocyanine dicyano or cyanoacetate derivative is present in an amount of 0.1 to 10% by weight based upon the total weight of the composition.

19. The composition according to claim 1, where the at least one dibenzoylmethane derivative is present in an amount of 0.1 to 10% by weight based upon the total weight of the composition and the at least one merocyanine dicyano or cyanoacetate derivative is present in an amount of 0.2 to 5% by weight based upon the total weight of the composition.

20. The composition according to claim 1, where the at least one dibenzoylmethane derivative is present in an amount of 0.1 to 6% by weight based upon the total weight of the composition and the at least one merocyanine dicyano or cyanoacetate derivative is present in an amount of 0.2 to 5% by weight based upon the total weight of the composition.

* * * * *